US009616058B2

(12) United States Patent
Cesar Castro Palomino Laria et al.

(10) Patent No.: US 9,616,058 B2
(45) Date of Patent: *Apr. 11, 2017

(54) POTENT SELECTIVE LSD1 INHIBITORS AND DUAL LSD1/MAO-B INHIBITORS FOR ANTIVIRAL USE

(75) Inventors: Julio Cesar Castro Palomino Laria, Premià de Mar, Barcelona (ES); Alberto Ortega Muñoz, Santa Coloma de Gramenet, Barcelona (ES); Nathalie Guibourt, Barcelona (ES); Jonathan Alleman Baker, Holladay, UT (US)

(73) Assignee: Oryzon Genomics, S.A., Cornellà de Llobregat, Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/580,553

(22) PCT Filed: Feb. 24, 2011

(86) PCT No.: PCT/US2011/026141
§ 371 (c)(1),
(2), (4) Date: Jan. 4, 2013

(87) PCT Pub. No.: WO2011/106574
PCT Pub. Date: Sep. 1, 2011

(65) Prior Publication Data
US 2013/0274267 A1 Oct. 17, 2013

Related U.S. Application Data

(60) Provisional application No. 61/338,935, filed on Feb. 24, 2010.

(51) Int. Cl.
*A61K 31/135* (2006.01)
*A61K 31/131* (2006.01)
*A61K 31/137* (2006.01)
*A61K 31/15* (2006.01)
*A61K 31/495* (2006.01)
*A61K 31/13* (2006.01)
*A61K 31/16* (2006.01)
*A61K 31/40* (2006.01)
*A61K 31/505* (2006.01)
*A61K 45/06* (2006.01)
*A61K 31/165* (2006.01)

(52) U.S. Cl.
CPC ............ *A61K 31/495* (2013.01); *A61K 31/13* (2013.01); *A61K 31/135* (2013.01); *A61K 31/16* (2013.01); *A61K 31/165* (2013.01); *A61K 31/40* (2013.01); *A61K 31/505* (2013.01); *A61K 45/06* (2013.01)

(58) Field of Classification Search
None
See application file for complete search history.

(56) References Cited

U.S. PATENT DOCUMENTS

| | | |
|---|---|---|
| 3,106,578 A | 10/1963 | Kaiser et al. |
| 3,365,458 A | 1/1968 | Biel et al. |
| 3,471,522 A | 10/1969 | Biel et al. |
| 3,532,712 A | 10/1970 | Biel et al. |
| 3,532,749 A | 10/1970 | Biel et al. |
| 3,758,684 A | 9/1973 | Elion et al. |
| 4,409,243 A | 10/1983 | Lieb |
| 4,522,811 A | 6/1985 | Eppstein et al. |
| 4,530,901 A | 7/1985 | Weissmann |
| 6,043,393 A | 3/2000 | de Meijere et al. |
| 6,211,244 B1 | 4/2001 | Van Wagenen et al. |
| 6,337,074 B1 | 1/2002 | Marsden et al. |
| 6,809,120 B1 | 10/2004 | Warrington et al. |
| 7,399,825 B2 | 7/2008 | Lipps et al. |
| 7,611,704 B2 | 11/2009 | Thorpe et al. |
| 7,628,993 B2 | 12/2009 | Vilalta et al. |
| 7,799,782 B2 | 9/2010 | Munson et al. |
| 8,524,717 B2 | 9/2013 | Guibourt et al. |
| 8,722,743 B2 | 5/2014 | Ortega-Munoz et al. |
| 9,186,337 B2 * | 11/2015 | Baker .................. A61K 31/131 |
| 2003/0008844 A1 | 1/2003 | Spero et al. |
| 2003/0236225 A1 | 12/2003 | Protopopova et al. |
| 2004/0019117 A1 | 1/2004 | Protopopova et al. |
| 2004/0033986 A1 | 2/2004 | Protopopova et al. |
| 2004/0048802 A1 | 3/2004 | Ripka et al. |
| 2004/0132820 A1 | 7/2004 | Gosselin et al. |
| 2004/0147741 A1 | 7/2004 | Sundermann et al. |

(Continued)

FOREIGN PATENT DOCUMENTS

| | | |
|---|---|---|
| EP | 1193268 | 4/2002 |
| EP | 1704859 | 9/2006 |

(Continued)

OTHER PUBLICATIONS

Ueda et al. Identification of cell-active lysine specific demethylase 1-selective inhibitors. J. Am. Chem. Soc. 2009, 131; 17536-17537.*
Liang et al. Inhibition of the histone demethylase LSD1 blocks alpha-herpesvirus lytic replication and reactivation from latency. Nature Medicine. vol. 15, No. 11, Nov. 2009.*
Soler et al. Detection of mucosal human papillomavirus types 6/11 in cutaneous lesiosn from transplant recipients. J. Invest. Dermatol. 101: 286-291, 1993.*
Ahmed et al, "Ticagrelor: a new reversible oral antiplatelet agent" Int Research Journal of Pharmacy, 2010, 1(1), 62-69.
Arya et al, "Synthesis of 5H-dibenzo[a,d]cycloheptene derivatives with diverse biological activities", Indian J Chemistry B, 1978, 16B,220-225.
Bar-Am et al, "Regulation of Bcl-2 family proteins, neurotrophic factors, and APP processing in the neurorescue activity of propargylamine". FASEB J, 2005, 19(13),1899-1901.

(Continued)

*Primary Examiner* — Anna Pagonakis
(74) *Attorney, Agent, or Firm* — Finnegan, Henderson, Farabow, Garrett & Dunner, LLP

(57) ABSTRACT

The present invention relates to the use of potent selective LSD inhibitors and LSD/MAO-B inhibitors for treating or preventing viral infections. Furthermore, the present invention relates to the new use of cyclopropylamine acetamide derivatives or cyclopropylamine derivatives, as defined herein, for treating or preventing viral infection and treating or preventing reactivation of a virus after latency.

9 Claims, No Drawings

(56) References Cited

U.S. PATENT DOCUMENTS

| | | | |
|---|---|---|---|
| 2004/0162287 A1 | 8/2004 | Sundermann et al. |
| 2004/0176469 A1 | 9/2004 | Thomas |
| 2004/0229872 A1 | 11/2004 | Friderichs et al. |
| 2004/0254158 A1 | 12/2004 | Qiao et al. |
| 2005/0009832 A1 | 1/2005 | Sun et al. |
| 2005/0154056 A1 | 7/2005 | Yang et al. |
| 2006/0116370 A1 | 6/2006 | Dollinger et al. |
| 2006/0148904 A1 | 7/2006 | Protopopova et al. |
| 2006/0211709 A1 | 9/2006 | Buhr et al. |
| 2006/0270673 A1 | 11/2006 | Duggan et al. |
| 2006/0275366 A1 | 12/2006 | Malcom et al. |
| 2006/0287287 A1 | 12/2006 | Gerritz et al. |
| 2007/0213338 A1 | 9/2007 | Lebsack et al. |
| 2008/0139665 A1 | 6/2008 | Schuele et al. |
| 2008/0242698 A1 | 10/2008 | Flor et al. |
| 2008/0269228 A1 | 10/2008 | Moore et al. |
| 2009/0203750 A1 | 8/2009 | Kozikowski et al. |
| 2009/0247530 A1 | 10/2009 | Nolte et al. |
| 2010/0016262 A1 | 1/2010 | Mehal et al. |
| 2010/0240649 A1 | 9/2010 | Zhang |
| 2010/0292225 A1 | 11/2010 | Chamoin et al. |
| 2010/0324147 A1 | 12/2010 | McCafferty et al. |
| 2012/0202810 A1 | 8/2012 | Nolte et al. |
| 2013/0095067 A1* | 4/2013 | Baker et al. ............. 424/85.4 |
| 2013/0197095 A1 | 8/2013 | Nolte et al. |

FOREIGN PATENT DOCUMENTS

| | | | |
|---|---|---|---|
| EP | 1741708 | 1/2007 | |
| EP | 2233495 | 9/2010 | |
| GB | 1307341 | 2/1973 | |
| JP | 2001354563 | 12/2001 | |
| SU | 230169 | 10/1968 | |
| WO | WO94/27947 | 12/1994 | |
| WO | WO96/38141 | 12/1996 | |
| WO | WO98/18459 | 5/1998 | |
| WO | WO99/05142 | 2/1999 | |
| WO | WO99/05143 | 2/1999 | |
| WO | WO99/31072 | 6/1999 | |
| WO | WO99/54440 | 10/1999 | |
| WO | WO99/67203 | 12/1999 | |
| WO | WO00/34283 | 6/2000 | |
| WO | WO01/92264 | 12/2001 | |
| WO | WO02/079152 | 10/2002 | |
| WO | WO03/087064 | 10/2003 | |
| WO | WO03/093297 | 11/2003 | |
| WO | WO03/096989 | 11/2003 | |
| WO | WO2004/020415 | 3/2004 | |
| WO | WO2004/055010 | 7/2004 | |
| WO | WO2004/062601 | 7/2004 | |
| WO | WO2004/065367 | 8/2004 | |
| WO | WO2004/072086 | 8/2004 | |
| WO | WO2005/009941 | 2/2005 | |
| WO | WO2005/023761 | 3/2005 | |
| WO | WO2005/025558 | 3/2005 | |
| WO | WO2005/037843 | 4/2005 | |
| WO | WO2005/058808 | 6/2005 | |
| WO | WO2005/058883 | 6/2005 | |
| WO | WO2005/058884 | 6/2005 | |
| WO | WO2005/103003 | 11/2005 | |
| WO | WO2006/071608 | 7/2006 | |
| WO | WO2006/087206 | 8/2006 | |
| WO | WO2007/000248 | 1/2007 | |
| WO | WO2007/005896 | 1/2007 | |
| WO | WO2007/015824 | 2/2007 | |
| WO | WO2007/025144 | 3/2007 | |
| WO | WO2007/025709 | 3/2007 | |
| WO | WO2007/021839 | 7/2007 | |
| WO | WO2007/106016 | 9/2007 | |
| WO | WO2007/134799 | 11/2007 | |
| WO | WO2008/033466 | 3/2008 | |
| WO | WO2008/116156 | 9/2008 | |
| WO | WO2008/127734 | 10/2008 | |
| WO | WO2009/001132 | 12/2008 | |
| WO | WO2009/023179 | 2/2009 | |
| WO | WO2009/039134 | 3/2009 | |
| WO | WO2009/052078 | 4/2009 | |
| WO | WO2009/097278 | 8/2009 | |
| WO | WO2009/109991 | 9/2009 | |
| WO | WO2009/117515 | 9/2009 | |
| WO | WO2009/145856 | 12/2009 | |
| WO | WO2009/153197 | 12/2009 | |
| WO | WO 2010/011845 | * 1/2010 | |
| WO | WO2010/014921 | 2/2010 | |
| WO | WO2010/030592 | 3/2010 | |
| WO | WO 2010/043721 | * 4/2010 | |
| WO | WO2010/043721 | 4/2010 | |
| WO | WO2010/084160 | 7/2010 | |
| WO | WO2010/085749 | 7/2010 | |
| WO | WO2010/099527 | 9/2010 | |
| WO | WO2010/139784 | 12/2010 | |
| WO | WO2010/143582 | 12/2010 | |
| WO | WO2011/022489 | 2/2011 | |
| WO | WO2011/031934 | 3/2011 | |
| WO | WO 2011/035941 | * 3/2011 | |
| WO | WO2011/042217 | 4/2011 | |
| WO | WO2011/057262 | 5/2011 | |
| WO | WO2011/106105 | 9/2011 | |
| WO | WO2011/106106 | 9/2011 | |
| WO | WO2011/113005 | 9/2011 | |
| WO | WO2011/131576 | 10/2011 | |
| WO | WO2011/131697 | 10/2011 | |
| WO | WO2011/132083 | 10/2011 | |
| WO | WO2012/001531 | 1/2012 | |
| WO | WO2012/013727 | 2/2012 | |
| WO | WO2012/013728 | 2/2012 | |
| WO | WO2012/034116 | 3/2012 | |
| WO | WO2012/042042 | 4/2012 | |
| WO | WO2012/045883 | 4/2012 | |
| WO | WO2012/072713 | 6/2012 | |
| WO | WO2012/107498 | 8/2012 | |
| WO | WO2012/107499 | 8/2012 | |
| WO | WO2012/135113 | 10/2012 | |
| WO | WO2012/156531 | 11/2012 | |
| WO | WO2012/156537 | 11/2012 | |
| WO | WO2013/057320 | 4/2013 | |
| WO | WO2013/057322 | 4/2013 | |

OTHER PUBLICATIONS

Barlesi et al, "Global histone modifications predict prognosis of resected non small-cell lung cancer",J Clin Oncol,2007,25, 4358-4364.

Benelkebir et al, "Enantioselective synthesis of tranylcypromine analogues as lysine demethylase (LSD1) inhibitors", Bioorg Med Chem, 2011,19(12),3709-3716.

Biljak et al,"Platelet count, mean platelet volume and smoking status in stable chronic obstructive pulmonary disease", Platelets, 2011,22(6), 466-70.

Binda et al, "Biochemical, structural, and biological evaluation of tranylcypromine derivatives as inhibitors of histone demethylases LSD1 and LSD2", J Am Chem Soc,2010,132(19),6827-6833.

Bisi et al, "Multidrug resistance reverting activity and antitumor profile of new phenothiazine derivatives", Bioorg Med Chem, 2008, 16(13), 6474-6482.

Boilard et al, "Platelets amplify inflammation in arthritis via collagen-dependent microparticle production", Science, 2010,327(5965), 580-583.

Bolesov et al, "Cyclopropanes and cyclobutanes LXIX", Zhurnal Organicheskoi Khimii (English Translation), 1974, 10(10), 2122-2128.

Bolesov et al, "Cyclopropanes and cyclobutanes LXVIII. N-mono and N,N-disubstituted 1-amino-2-phenylcyclopropanes",Zhurnal Organicheskoi Khimii (English Translation), 1974, 10(6), 1678-84.

Brand and Perrimon, "Targeted gene expression as a means of altering cell fates and generating dominant phenotypes", 1993, Development, 118, 401-415.

Brydon et al, "Platelets, coronary heart disease and stress", Brain, Behavior and Immunity,2006, 20(2), 113-119.

Burakova et al, "N- and O-alkylation of 3-indolylcyclopropylacetic acid derivatives", Russian Chemical Bulletin, 2002, 51(10) 1829-1840.

(56) References Cited

OTHER PUBLICATIONS

Burk et al, "Cognitive deficits in spinocerebellar ataxia 2", Brain, 1999,122(4), 769-777.
Cakmak et al, "Platelets: indicator of inflammation in COPD", Int J Med Med Sci, 2009, 1(5), 227-229.
Calogero et al, "Inhibition of cell growth by EGR-1 in human primary cultures from malignant glioma",Cancer Cell International,2004,4, 1.
Casero et al, "Recent advances in the development of polyamine analogues as antitumor agents", J Med Chem, 2009, 52(15),4551-4573.
Chen et al, "Association of insulin resistance and hematologic parameters: study of a middle-aged and elderly chinese population in Taiwan", J Chin Med Assoc,2006, 69(6), 248-253.
Chimenti et al "Synthesis, Stereochemical Identification, and Selective Inhibitory Activity against Human Monoamine Oxidase-B of 2-Methylcyclohexylidene-(4-arylthiazol-2-yl)hydrazones", (2008) J. Med. Chem. 51 (15), 4874-4880.
Choi et al "Histone demethylase LSD1 is required to induce skeletal muscle differentiation by regulating myogenic factors" (2010) Biochemical and Biophysical Research Communications 401(3), 327-332.
Choo et al, "Genetic organization and diversity of the hepatitis C virus", Proc Natl Acad Sci,1991, 88,2451-2455.
Culhane et al, A mechanism-based inactivator for histone demethylase LSD1, J Am Chem Soc, 2006, 128(14), 4536-4537.
Culhane et al, "Comparative analysis of small molecules and histone substrate analogues as LSD1 lysine demethylase inhibitors", J Am Chem Soc, 2010,132(9),3164-3176.
Danese et al, "Platelets in inflammatory bowel disease: clinical, pathogenic and therapeutic implications", Am J Gastroenterol, 2004,99(5), 938-45.
Di Stefano et al, Mutation of *Drosophila* Lsd1 disrupts H3-K4 methylation, resulting in tissue-specific defects during development, Curr Biol,2007, 17(9), 808-12.
East et al, "An orally bioavailable positive allosteric modulator of the mGlu4 receptor with efficacy in an animal model of motor dysfunction", Bioorg Med Chem Lett, 2010, 20(16), 4901-5.
Ellis et al, "Expression of *Drosophila* glass protein and evidence for negative regulation of its activity in non-neuronal cells by another DNA-binding protein",Development,1993, 119, 855-865.
Elsheikh et al "Global histone modifications in breast cancer correlate with tumor phenotypes, prognostic factors and patient outcome", Canc Res, 2009,69, 3802-3809.
Erazo et al, "Varicella-zoster virus open reading frame 66 protein kinase is required for efficient viral growth in primary human corneal stromal fibroblast cells", J Virol, 2008,82, 7653-7665.
Faler et al, "The Kulinkovich reaction in the synthesis of constrained N,N-dialkyl neurotransmitter analogues", Organic Letters 2007,9(10),1987-1990.
Ferlay et al, "Estimates of the cancer incidence and mortality in Europe in 2006", Annals of Oncology 2007,18(3), 581-92.
Ferraro et al, "EGR1 predicts PTEN and survival in patients with non-small-cell lung cancer", J Clin Oncol, 2005, 23(9), 1921-26.
Fischer et al, "Recovery of learning and memory is associated with chromatin remodelling", Nature, 2007,447, 178-182.
Forneris et al "LSD1: oxidative chemistry for multifaceted functions in chromatin Regulation." Trends in Biochemical Sciences 2008,33(4), 181-189.
Gawaz et al, "Platelets in inflammation and atherogenesis", J Clin Invest, 2005,115(12), 3378-3384.
Gooden et al, "Facile synthesis of substituted trans-2-arylcyclopropylamine inhibitors of the human histone demethylase LSD1 and monoamine oxidases A and B", Bioorg Med Chem Lett 2008, 18(10), 3047-51.
Han et al "Modulation of breast cancer resistance protein (BCRP/ABCG2) by non-basic chalcone analogues" Eur. J. Pharma. 2008, 35(1-2) 30-41.

Han et al, "Antidepressants reveal differential effect against 1-methyl-4-phenylpyridinium toxicity in differentiated PC12 cells", Eur J Pharmacol, 2009, 604 (1-3),36-44.
Hayami et al, "Overexpression of LSD1 contributes to human carcinogenesis through chromatin regulation in various cancers", Int J Cancer, 2011, 128(3), 574-86.
Hruschka et al, "Fluorinated phenylcyclopropylamines, Part 5:Effect of electron-withdrawing or- donating aryl substituents on the inhibition of monoamine oxidases A and B by 2-aryl-2-fluorocyclopropylamines", Bioorg Med Chem,2008, 16(15), 7148-7166.
Huang et al, "Novel oligoamine analogues inhibit lysine-specific demethylase 1 (LSD1) and induce re-expression of epigeneticall silenced genes",Clin Cancer Res,2009, 15(23), 7217-28.
Huang et al, "p53 is regulated by the lysine demethylase LSD1",Nature,2007,449, 105-108.
Huang et al,"Inhibition of lysine-specific demethylase 1 by polyamine analogues results in reexpression of aberrantly silenced genes", PNAS,2007, 104(19), 8023-8028.
Jackson et al, "Polyglutamine-expanded human Huntingtin transgenes induce degeneration of *Drosophila* photoreceptor neurons", Neuron, 1998, 21, 633-642.
Kahl et al,"Androgen receptor coactivators lysine-specific histone demethylase 1 and four and a half LIM domain protein 2 predict risk of prostate cancer recurrence", Cancer Res,2006,66 (23), 11341-11347.
Kaiser et al, "2-substituted cyclopropylamines. I. Derivatives and analogs of 2-phenylcyclopropylamine", J Med Pharm Chem (ACS), 1962, 5, 1243-1265.
Kiefmann et al, "Red blood cells induce hypoxic lung inflammation", Blood, 2008,111(10),5205-14.
Kim et al, "Flavin chemical models for monoamine oxidase inactivation by cyclopropylamines, α-silylamines, and hydrazines", J Am Chem Soc 1995, 117, 100-105.
Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide), a potent smoothened antagonist for use in Hedgehog pathway dependent malignancies, Part 2", Bioorg Med Chem Lett 2011, 21(15), 4429-4435.
Kornerup et al, "The role of platelets in the pathophysiology of asthma" Platelets, 2007,18(5), 319-28.
Krieger et al, "Enhancement of hepatitis C virus RNA replication by cell culture-adaptive mutations", J Virol, 2001,75, 4614-4624.
Lan et al "Mechanisms involved in the regulation of histone lysine demethylases". Current Opinion in Cell Biology, 2008,20, 316-325.
Lee et al, "Combinatorial lead optimization of [1,2]-diamines based on ethambutol as potential antituberculosis preclinical candidates", J Comb Chem, 2003, 5(2), 172-187.
Lee et al, "Histone H3 lysine 4 demethylation is a target of nonselective antidepressive medications",Chem Biol, 2006,13(6), 563-567.
Li et al, "Association between inflammatory mediators and angiographic morphologic features indicating thrombus formation in patients with acute myocardial infarction", Chin Med J, 2009,122(15), 1738-42.
Lim et al, "Lysine-specific demethylase 1 (LSD1) is highly expressed in ER-negative breast cancers and a biomarker predicting aggressive biology", Carcinogenesis,2010, 31(3), 512-20.
Lucerna et al, "Sustained expression of early growth response protein-1 blocks angiogenesis and tumor growth",Cancer Research,2006, 66,6708-6713.
Lupu Roxana, "Up-to-date in the hematological malignancies treatment", Maedica, 2006,1(1), 63-65.
Maclay et al, "Increased platelet activation in patients with stable and acute exacerbation of COPD", Thorax, 2011,66(9), 769-74.
Mannaioni et al, "Platelets and inflammation: role of platelet-derived growth factor, adhesion molecules and histamine", Inflamm Res, 1997,46(1), 4-18.
McNicol et al, "Beyond hemostasis: the role of platelets in inflammation, malignancy and infection",Cardiovascular & Haematological Disorders—Drug Targets, 2008,8, 99-117.
Meanwell, "Synopsis of some recent tactical application of bioisosteres in drug design", J Med Chem, 2011, 54(8),2529-91.

(56) References Cited

OTHER PUBLICATIONS

Metzger et al, "LSD1 demethylates repressive histone marks to promote androgen-receptor-dependent transcription",Nature,2005, 437(7057),436-9.

Mimasu et al "Crystal structure of histone demethylase LSD1 and tranylcypromine at 2.25 Å" Biochemical and Biophysical Research Communications ,2008,366, 15-22.

Mimasu et al, "Structurally designed trans-2-phenylcyclopropylamine derivatives potently inhibit histone demethylase LSD1/KDM1", Biochemistry,2010,49(30), 6494-6503.

Moritani et al, "Activation of platelets in bronchial asthma", Chest, 1998,113, 452-458.

Nabil Aboul-Enein et al, "Synthesis of some 4-substituted amino-1-methylpiperidines structurally related to antihistaminics", Pharmaceutica Acta Helvetiae, 1973, 48(3): 151-156.

Neelamegan et al, "Brain-penetrant LSD1 inhibitors can block memory consolidation", ACS Chem Neurosci, 2012, 3(2), 120-128.

Ogasawara et al, "Synthesis and biological activity of optically active NCL-1, a lysine-specific demethylase 1 selective inhibitor",Bioorg Med Chem, 2011, doi:10.1016/j.bmc.2010.12.024.

O'Sullivan et al, "The inflammatory role of platelets in cystic fibrosis", Am J Respir Crit Care Med, 2006,173, 483-90.

Pannala et al "Synthesis and structure-activity relationship of 4-(2-aryl-cyclopropylamino)-quinoline-3-carbonitriles as EGFR tyrosine kinase inhibitors", Bioorg & Med Chem Lett , 2007,17(21), 5978-5082.

Pitchford et al, "Platelet P-selectin is required for pulmonary eosinophil and lymphocyte recruitment in a murine model of allergic inflammation", Blood, 2005,105, 2074-2081.

Pollock et al, Lysine-specific histone demethylase 1 inhibitors control breast cancer proliferation in ERalpha-dependent and -independent manners, ACS Chem Biol 2012,7,1221-1231.

Ravina et al, "The relationship between CAG repeat length and clinical progression in Huntington's disease", Movement Disorders,2008,23(9), 1223-7.

Reddy et al, "Role of lysine-specific demethylase 1 in the proinflammatory phenotype of vascular smooth muscle cells of diabetic mice",Circ Res,2008,103, 615-23.

Riley et al, "Absolute configuration of (+)- and (−)-trans-2-phenylcyclopropylamine hydrochloride",J Med Chem, 1972,15(11), 1187-1188.

Rinder et al, "Correlation of thrombosis with increased platelet turnover in thrombocytosis", Blood, 1998,91(4), 1288-1294.

Schmidt et al,"trans-2-phenylcyclopropylamine is a mechanism-based inactivator of the histone demethylase LSD1", Biochemistry, 2007,46(14)4408-4416.

Schulte et al, "Lysine-specific demethylase 1 is strongly expressed in poorly differentiated neuroblastoma: implications for therapy", Cancer Res,2009,69(5),2065-71.

Scoumanne et al "Protein methylation: a new mechanism of p53 tumor suppressor regulation" Histol Histopathol 2008,23, 1143-1149.

Scoumanne et al, "The lysine-specific demethylase 1 is required for cell proliferation in both p53-dependent and -independent manners", J Biol Chem, 2007,282(21), 15471-5.

Seligson et al, "Global histone modification patterns predict risk of prostate cancer recurrence",Nature, 2005,435, 1262-1266.

Seligson et al,"Global levels of histone modifications predict prognosis in different cancers" ,Am J Path, 2009,174,1619-28.

Sharma et al, "(Bis)urea and (bis)thiourea inhibitors of lysine-specific demethylase 1 as epigenetic modulators", J Med Chem, 2010,53(14), 5197-5212.

Shi et al,"Histone demethylation mediated by the nuclear amine oxidase homolog LSD1", Cell, 2004,119,941-953.

Shi, "Histone lysine demethylases: emerging roles in development, physiology and disease", Nature Reviews Genetics 2007, 8:829-833.

Stephens et al, "The determination of the absolute configurations of chiral molecules using vibrational circular dichroism (VCD) spectroscopy",Chirality, 2008,20(5), 643-663.

Stoffel et al, "Leukocyte count and risk of thrombosis in patients undergoing haematopoietic stem cell transplantation or intensive chemotherapy",Thromb Haemost, 2010,103(6), 1228-32.

Stratmann et al, "Pathobiology and cell interactions of platelets in diabetes", Diabetes & Vascular Disease Research,2005, 2(1), 16-23.

Szewczuk et al, "Mechanistic analysis of a suicide inactivator of histone demethylase LSD1", Biochemistry, 2007,46, 6892-6902.

Tamagawa-Mineoka et al, "Elevated platelet activation in patients with atopic dermatitis and psoriasis: increased plasma levels of beta-thromboglobulin and platelet factor 4", Allergology International,2008, 57, 391-396.

Taylor et al,"Roscovitine, a cyclin-dependent kinase inhibitor, prevents replication of varicella-zoster virus", J Virol, 2004,78, 2853-2862.

Thaulow et al, "Blood platelet count and function are related to total and cardiovascular death in apparently healtht men", Circulation, 1991,84, 613-617.

Vagner et al, "Peptidomimetics, a synthetic tool of drug discovery", Current Opinion on Chemical Biology, 2008, 12:292-296.

Wagner et al, "Platelets in inflammation and thrombosis", Arteriosclerosis, Thrombosis and Vascular Biology, 2003,23, 2131-2137.

Wang et al, Novel histone demethylase LSD1 inhibitors selectively target cancer cells with pluripotent stem cell properties, Cancer Research, 2011, 71(23):7238-49.

Wang et al "LSD1 is a Subunit of the NuRD Complex and Targets the Metastasis Programs in Breast Cancer" Cell 2009, 138, 660-672.

Wang et al, "The lysine demethylase LSD1 (KDM1) is required for maintenance of global DNA methylation", Nature Genetics, 2009,41(1), 125-129.

Weinreb et al, "Novel neuroprotective mechanism of action of rasagiline is associated with its propargyl moiety: interaction of Bcl-2 family members with PKC pathway", Ann NY Acad Sci, 2005,1053, 348-55.

Wermuth, "Molecular variations based on isosteric replacements", The Practice of Medicinal Chemistry (2nd edition), Academic Press, London, 2003, pp. 189-214.

Westland et al , "N-substituted derivatives of 2-aminoethanethiol and 2-hydraxinoethanethiol", JMedChem 1968, 11(4),824-829.

Whitlow et al,"Recruitment of the transcriptional coactivator HCF-1 to viral immediate-early promoters during initiation of reactivation from latency of herpes simplex virus type 1", J Virol, 2009,83(18):9591-5.

Willoughby et al, "Platelets and cardiovascular disease",Eur J Cardiovasc Nursing,2002,1, 273-288.

XP002568777 Database chemcats, database accession No. 2088922753, order No. kbsb-0063197, Aurora screening library, Aug. 20, 2009.

Yang et al "Structural Basis for the inhibition of the LSD1 Histone Demethylase by the Antidepressant trans-2-Phenylcyclopropylamine" Biochemistry 2007,46 (27), 8058-8065.

Yang et al "Structural basis of histone demethylation by LSD1 revealed by suicide inactivation" Nature Structural & Molecular Biology 2007, 14(6), 535-539.

Yoshida et al, "Fluorinated phenylcyclopropylamines. Part 3: inhibition of monoamine oxidase A and B",Bioorg Med Chem,2004,12(10),2645-2652.

Youdim et al, "Bifunctional drug derivatives of MAO-B inhibitor rasagiline and iron chelator VK-28 as a more effective approach to treatment of brain ageing and ageing neurodegenerative diseases", Mechanisms of Ageing and Development, 2005, 126: 317-326.

F. Zaragoza Dorwald "Side reactions in Organic Synthesis: a guide to successful synthesis design" Wiley-VCH Verlag GmbH & Co, KGaA, Wilenheim, Chapter 1, 2005.

Zirkle et al, "2-substituted cyclopropylamines. II. Effect of structure upon monoamine oxidase-inhibitory activity as measured in vivo by potentiation of tryptamine convulsions", J Med Pharm Chem (ACS), 1962, 5, 1265-84.

"Definition of Cancer"—MedicineNetcom Medical references for patients, http://www.medterms.com, 2005.

(56) References Cited

OTHER PUBLICATIONS

Johnson et al, CAPLUS, Document No. 157:576967, "Preparation of cyclopropylamines as LSD1 inhibitors in the treatment of cancer", 2012.
Delorme et al, HCAPLUS, Document No. 132:49802, "Preparation of 1-(N-substituted aminomethyl)-4-guanidinomethylcyclohexanes useful in pain management", 1999.
CAS Registry No. RN220351-33-7, entered STN Mar. 11, 1999.
CAS Registry No. RN844655-03-4, entered STN Mar. 9, 2005.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN903487-42-3, entered STN Aug. 23, 2006.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
CAS Registry No. RN1218057-33-0, entered STN Apr. 11, 2010.
CAS Registry No. RN1247564-27-7, entered STN Oct. 27, 2010.
CAS Registry No. RN1247717-42-5, entered STN Oct. 27, 2010.
CAS Registry No. RN1247999-77-4, entered STN Oct. 28, 2010.
CAS Registry No. RN1248611-33-7, entered STN Oct. 29, 2010.
CAS Registry No. RN1248913-30-5, entered STN Nov. 1, 2010.
CAS Registry No. RN1248971-98-3, entered STN Nov. 1, 2010.
CAS Registry No. RN1250045-89-6, entered STN Nov. 1, 2010.
CAS Registry No. RN1250199-20-2, entered STN Nov. 1, 2010.
CAS Registry No. RN1250332-49-0, entered STN Nov. 1, 2010.
CAS Registry No. RN1251130-23-0, entered STN Nov. 3, 2010.
Co-pending U.S. Appl. No. 13/138,143, filed Jul. 11, 2011.
Co-pending U.S. Appl. No. 13/497,994, filed Mar. 23, 2012.
Co-pending U.S. Appl. No. 13/500,687, filed Apr. 6, 2012.
Co-pending U.S. Appl. No. 13/580,710, filed Aug. 23, 2012.
Co-pending U.S. Appl. No. 13/812,366, filed Jan. 25, 2013.
Co-pending U.S. Appl. No. 13/812,386, filed Jan. 25, 2013.
Co-pending U.S. Appl. No. 13/876,485, filed Mar. 28, 2013.
Co-pending U.S. Appl. No. 13/877,919, filed Apr. 5, 2013.
Co-pending U.S. Appl. No. 13/983,844, filed Aug. 6, 2013.
Co-pending U.S. Appl. No. 14/118,323, filed Nov. 18, 2013.
Co-pending U.S. Appl. No. 14/118,330, filed Nov. 18, 2013.
Co-pending U.S. Appl. No. 14/096,557, filed Dec. 4, 2013.
Co-pending U.S. Appl. No. 14/184,745, filed Feb. 20, 2014.
Co-pending U.S. Appl. No. 14/228,083, filed Mar. 27, 2014.
Co-pending U.S. Appl. No. 14/352,719, filed Apr. 18, 2014.
Co-pending U.S. Appl. No. 14/352,711, filed Apr. 18, 2014.
Co-pending U.S. Appl. No. 14/480,765, filed Sep. 9, 2014.
International Search Report and Written Opinion of the International Searching Authority for PCT/US2011/026141, dated Nov. 3, 2011.

\* cited by examiner

POTENT SELECTIVE LSD1 INHIBITORS AND DUAL LSD1/MAO-B INHIBITORS FOR ANTIVIRAL USE

PRIORITY CLAIM

This application claims the benefit of the filing date of U.S. Provisional Patent Application Ser. No. 61/338,935, filed Feb. 24, 2010, for "INHIBITORS FOR ANTIVIRAL USE," the entire disclosure of which is hereby incorporated herein by this reference.

TECHNICAL FIELD

The invention relates to compounds for preventing or treating viral infections.

BACKGROUND

Viruses are a problem across the world, causing many of the diseases that afflict individuals today. Virus infections both in man and in animals have long presented a serious problem to which no wholly satisfactory answer has been found.

Some viral infections may be due to herpes infections. The herpesviruses are classified as, e.g., herpes simplex virus type 1 (HSV-1) or type 2 (HSV-2), varicella zoster virus (VZV), Epstein-Barr virus (EBV), cytomegalovirus (CMV), roseolovirus or rhadinovirus.

Herpes simplex viruses (HSV) type 1 and type 2 are double stranded DNA viruses. The clinical entities attributable to HSV-1 include the following: (1) Acute herpetic gingivostomatitis which occurs mostly in small children; (2) Eczema herpeticum-Kaposi's varicelliform eruption which can sometimes be fatal; (3) Keratoconjunctivitis infection of the eye, with recurrent infection, which can lead to permanent opacification and blindness; (4) Herpes encephalitis which carries a high mortality rate and the survivors often have residual neurological defects; and (5) Herpes labilis, which present as cold sores and are most common recurrent disease in the form of oral lesions.

HSV-2 is implicated in the following: (1) Genital herpes or herpes progenitalis, which is characterized by vesiculoulcerative lesions of the penis or the cervix, vulva and vagina; (2) Neonatal herpes is a form of herpes that can be transmitted to the newborn during birth by contact with herpetic lesions in the birth canal if the mother is infected with the virus and sometimes can produce permanent brain damage.

Varicella zoster virus is a double-stranded DNA virus and it is morphologically identical with herpes simplex viruses. It is a causative agent for shingles in adults which is characterized by an inflammatory reaction of the posterior nerve roots and ganglia, accompanied by the affected sensory nerves. Varicella zoster virus (VZV) infection results in chickenpox (varicella), which may rarely result in complications including encephalitis or pneumonia. Even when clinical symptoms of chickenpox have resolved, VZV remains dormant in the nervous system of the infected person (virus latency), in the trigeminal and dorsal root ganglia. In about 10-20% of cases, VZV reactivates later in life producing a disease known as herpes zoster or shingles. Serious complications of shingles include post-herpetic neuralgia, zoster multiplex, myelitis, herpes ophthalmicus, or zoster sine herpete.

The symptoms of EBV infection in children can be indistinguishable from the symptoms of other typical childhood illnesses. Individuals not infected as a child have a risk of being infected during adolescence or young adulthood, which often causes infectious mononucleosis (mono). Diseases caused by EBV are particularly common among people with reduced immunity. EBV is associated with a tumor often found in organ transplant patients, which is referred to as post-transplant lymphoproliferative disease.

Typical antiviral medications used against herpes viruses work by interfering with viral replication, effectively slowing the replication rate of the virus and providing a greater opportunity for the immune response to intervene. Current treatments for human herpesviruses include acyclovir, cidofovir, famciclovir, doxorubicin and other pharmaceuticals. Moreover, amino purine derivatives have been disclosed in U.S. Pat. No. 3,758,684 to treat DNA virus infections and U.S. Pat. No. 7,628,993 covers DNA vaccines targeting a specific HSV-2 protein. U.S. Pat. No. 6,337,074 discloses peptides which disrupting the association of two viral proteins required for DNA replication in herpesviruses. U.S. Pat. No. 7,399,825 discloses peptides which inhibit infectivity of DNA viruses.

The vaccine Herpevac against HSV-2 has only been shown to be effective for women who have never been exposed to HSV-1. Overall, the vaccine is approximately 48% effective in preventing HSV-2 seropositivity and about 78% effective in preventing symptomatic HSV-2. During initial trials, the vaccine did not exhibit any evidence of preventing HSV-2 in males.

U.S. Pat. No. 7,611,704 covers compositions and methods of treating virus infections using Bavituximab and similar antibodies. Bavituximab is a PS-targeting antibody, the antibody's binding to phospholipids alerts the body's immune system to attack the tumor endothelial cells, thrombosing the tumor's vascular network and/or attacking free floating virally infected and metastatic cells while potentially minimizing side effects in healthy tissues.

Antiviral medications can reduce the frequency, duration, and severity of outbreaks. However, these infections are difficult to treat, treatments are not effective for all patients and there is no cure that can eradicate herpes virus from the body. Therefore, currently, there is no effective treatment against the infections caused by human herpesviruses and improved methods for treatment are being sought. Furthermore, viruses can become resistant to current treatments so there is a need to find new antiviral agents having new mechanisms of action.

Recent work published in *Nature Medicine* found that the host enzyme LSD1 interacts with a key host protein (HCF-1) that the herpesviruses require to infect host cells. Herpes viruses lack their own RNA polymerase and require the use of a host. To prepare a host for viral gene transcription, α-herpesviruses need to increase methylation of histone H3Lys4 (H3K4) and decrease methylation of H3K9. Researchers reported in *Nature Medicine* that to decrease the methylation, the demethylase called lysine-specific demethylase-1 (LSD1) is required. LSD1 interacts with the host cell factor-1 (HCF-1) component of the histone methyltransferase complex. Moreover, blocking LSD1 activity using monoamine oxidase inhibitors (MAOIs), which are known to target LSD1, led to inhibition of viral gene transcription. Researchers noticed when levels of LSD 1 are reduced the corresponding levels of HSV and VZV mRNA and proteins decreased. This discovery suggest a new way to attack virus infections, inhibiting LSD1, the virus host's transcriptional machinery to produce viral mRNA is stopped, therefore decreasing the ability of α-herpesvirus to express the viral genes necessary to continue infection.

Lysine Specific Demethylase-1 (LSD1) has a fair degree of structural similarity, and amino acid identity/homology to monoamine oxidases. It was recently found that some compounds which target monoamine oxidase (MAO), also inhibit LSD 1 at clinically relevant concentrations (Lee et al. (2006) Chem. Biol. 13:563-567, Schmidt et al. (2007) Biochemistry 46(14)4408-4416) and Gooden et al. (2008) Bioorg. Med. Chem. Let. 18:3047-3051).

WO 2010/011845 discloses inhibitors of LSD 1 and/or MAOs inhibitors for treating or preventing viral infections. However, the disclosed inhibitors are known to inhibit MAO enzymes more strongly than LSD 1 and moreover, they indistinctly inhibited MAOs. Since MAO-A inhibitors can cause dangerous side-effects (see e.g., Yoshida et al. (2004) Bioorg. Med. Chem. 12(10):2645-2652; Hruschka et al. (2008) Biorg Med. Chem. (16):7148-7166; Folks et al. (1983) J. Clin. Psychopharmacol. (3)249; and Youdim et al. (1983) Mod. Probl. Pharmacopsychiatry (19):63) selective LSD1/MAO-B dual inhibitors present an important advantage.

Furthermore, most of the LSD1 selective inhibitors of the prior art Ki (IC50) parameters higher than 1 µM for LSD1. Without intending being bound by any theory, the inventors believe that more efficient selective LSD1 inhibitors can have better results when used as antiviral, which could implicate lower doses and less side effects. Additional dual LSD1/MAO-B inhibitors can avoid the side-effects associated with inhibition of MAO-A.

Although the foregoing methods have advanced the art of antiviral treatment, the development of additional or alternative targeting therapies is still sought. The development of new drugs that prevent or treat viral infection of a host by inhibiting novel targets, particularly those which selectively inhibit LSD1 and LSD 1/MAO-B is an importance advance. In view of the good LSD1 and LSD1/MAO-B-selective inhibition of the novel "cyclopropylamine acetamide" derivatives and "cyclopropylamine" derivatives, these represent a new class of compounds for preventing or treating viral infections with novel mechanisms of action.

DISCLOSURE

The present invention relates to the use of potent selective LSD1 inhibitors and LSD1/MAO-B inhibitors for treating or preventing viral infections. Furthermore, the present invention relates to the new use of cyclopropylamine acetamide derivatives or cyclopropylamine derivatives, as defined herein, for treating or preventing viral infection and treating or preventing reactivation of a virus after latency.

In one embodiment, the present invention relates to a method of treating or preventing a viral infection in a host. The method of this embodiment comprises administering to the host an effective amount of a potent selective inhibitor of LSD1 or a pharmaceutically acceptable salt thereof. In a more specific aspect, the method of this embodiment further comprises identifying a patient in need of such treatment or prevention.

In one embodiment, the present invention relates to a method of treating or preventing a viral infection. The method of this embodiment comprises administering to a host an effective amount of a LSD1/MAO-B dual inhibitor or a pharmaceutically acceptable salt thereof. In a more specific aspect, the method of this embodiment further comprises identifying a patient in need of such treatment or prevention.

In one embodiment, the present invention relates to a method of treating or preventing reactivation of a virus after latency. The method of this embodiment comprises administering to the host an effective amount of a potent selective inhibitor of LSD1 or a pharmaceutically acceptable salt thereof. In a more specific aspect, the method of this embodiment further comprises identifying a patient in need of such treatment or prevention.

In one embodiment, the present invention relates to a method of treating or preventing reactivation of a virus after latency. The method of this embodiment comprises administering to a host an effective amount of a LSD1/MAO-B dual inhibitor or a pharmaceutically acceptable salt thereof. In a more specific aspect, the method of this embodiment further comprises identifying a patient in need of such treatment or prevention.

In another embodiment, the present invention relates to a method of treating or preventing viral infection. The method of this embodiment comprises administering to a host an effective amount of a cyclopropylamine acetamide derivative or a cyclopropylamine derivative. In a more specific aspect, the method of this embodiment further comprises identifying a patient in need of such treatment or prevention.

Another embodiment of the invention relates to a method of preventing or treating reactivation of a virus after latency in a host. The method of this embodiment by administering an effective amount of a cyclopropylamine acetamide derivative or a cyclopropylamine derivative. In a more specific aspect, the method of this embodiment further comprises identifying a patient in need of such treatment or prevention.

Another embodiment of the invention provides a method of preventing or treating a viral infection in a mammal that has undergone, is undergoing, or will undergo an organ or tissue transplant. The method of this embodiment comprises administering to the mammal an effective amount of a potent selective LSD1 inhibitor or a dual LSD1/MAO-B inhibitor before, during, and/or after the organ or tissue transplant. In a more specific aspect, the method of this embodiment further comprises identifying a patient in need of such treatment or prevention.

Another embodiment of the invention provides a method of preventing or treating a viral infection in a mammal that has undergone, is undergoing, or will undergo an organ or tissue transplant. The method of this embodiment comprises administering to the mammal an effective amount of a cyclopropylamine acetamide derivative or a cyclopropylamine derivative before, during, and/or after the organ or tissue transplant. In a more specific aspect, the method of this embodiment further comprises identifying a patient in need of such treatment or prevention.

The invention also relates to pharmaceutical compositions suitable for topical administration comprising pharmaceutically acceptable carrier suitable for topical administration and a compound chosen from a potent selective LSD1 inhibitor, LSD1/MAO-B dual inhibitor, cyclopropylamine acetamide derivative, and cyclopropylamine derivative. In one aspect the compound is a potent selective LSD1 inhibitor. In one aspect the compound is a LSD1/MAO-B dual inhibitor. In one aspect the compound is a cyclopropylamine acetamide derivative. In one aspect the compound is a cyclopropylamine derivative.

In one embodiment, the invention provides a method of treating HIV in an individual co-infected with a herpes simplex virus 2. According to this embodiment an individual having HIV and co-infected with herpes simplex virus 2 is administered a compound selected from a selective potent LSD1 inhibitor, a dual LSD1/MAO-B inhibitor, a cyclopropylacetamide derivative, and a cyclopropylamine derivative.

In one aspect of this embodiment, the individual is administered one or more additional antiviral drugs wherein said one or more additional antiviral drugs is suitable for treating HIV.

Thus, in specific aspects, the invention is:

A method of treating or preventing a viral infection, comprising administering to a host a therapeutically effective amount of a selective potent LSD 1 inhibitor or a LSD1/MAO-B dual inhibitor or a pharmaceutically acceptable salt thereof.

A method of treating or preventing reactivation of a virus after latency in a host comprising administering a therapeutically effective amount of a potent LSD1 inhibitor or a LSD1/MAO-B dual inhibitor or a pharmaceutically acceptable salt thereof.

A method of treating or preventing viral infections in a mammal that has undergone, is undergoing or will undergo an organ or tissue transplant comprising administering a therapeutically effective amount of a potent LSD1 inhibitor or a LSD1/MAO-B dual inhibitor or a pharmaceutically acceptable salt thereof.

The method as in one of 1, 2 or 3, wherein the potent LSD1 inhibitor or LSD1/MAO-B dual inhibitor is a cyclopropylamine acetamide derivative or a cyclopropylamine derivative.

The method as in one of 1, 2, 3 or 4, wherein the antiviral compound is administered with a pharmaceutically acceptable carrier.

The method as in one of 1, 2, 3 or 4 or a pharmaceutically acceptable solvate thereof, alone or in association with other active principles, in the manufacture of a medicament useful for the treatment or prevention of viral infections.

The method as in one of 1, 2, 3 or 4, wherein the host is a mammal.

The method as in 7, wherein the host is a human.

The method as in one of 1, 2, 3 or 4, wherein the viral infection is caused by a virus chosen from a herpesvirus, adenovirus, human papilloma virus, parvovirus B19, smallpox virus, vaccinia virus, hepatitis B virus, polyoma virus, JC virus or a transfusion transmitted virus.

The method as in one of 1, 2, 3 or 4, wherein the viral infection is caused by a herpesvirus or adenovirus.

The method as in one of 1, 2, 3 or 4, alone or in combination with one or more additional antiviral compounds, in the manufacture of a medicament useful for the treatment or prevention of viral infection.

The method as in one of 1, 2, 3 or 4, wherein the virus or viral infection is HSV1 or HSV1 infection.

The method as in one of 1, 2, 3 or 4, wherein the virus or viral infection is HSV2 or HSV2 infection.

The method as in one of 1, 2, 3 or 4, wherein the virus or viral infection is EBV or an EBV infection.

The method as in one of 1, 2, 3 or 4, wherein the virus or viral infection is VZV or a VZV infection.

The method as in one of 1, 2, 3 or 4, wherein the virus or viral infection is CMV or a CMV infection.

The method as in one of 1, 2, 3 or 4, wherein the virus or viral infection is an adenovirus or adenovirus infection.

A method of treating HIV in an individual co-infected with a herpes simplex virus 2 comprising identifying an individual having HIV and co-infected with herpes simplex virus 2 and administering to said individual a compound which is a selective potent LSD1 inhibitor, a dual LSD1/MAO-B inhibitor, a cyclopropylacetamide derivative, or a cyclopropylamine derivative, thereby treating HIV.

The method as in 17, wherein the individual is administered one or more additional antiviral drugs wherein said one or more additional antiviral drugs is suitable for treating HIV.

MODE(S) FOR CARRYING OUT THE INVENTION

The present invention relates to the use of potent selective LSD1 inhibitors and LSD1/MAO-B dual inhibitors for treating or preventing viral infections. Furthermore, the present invention relates to the new use of cyclopropylamine acetamide derivative or cyclopropylamine derivative, as defined herein, for treating or preventing viral infections.

Without intending to be bound by any theory, it is believed that the compounds provided herein are particularly useful in the treatment and/prevention of viral infections because they efficiently interfere with LSD1 and/or MAO-B activity (i.e., inhibit LSD1 activity). It is known in the art that viruses co-opt some biochemical machinery of their host to replicate. To the extent that the virus co-opts LSD1, protein complexes containing LSD1, a gene or genes whose expression is regulated by LSD1 or a protein complex containing LSD1, or signaling pathways related to LSD1, for replication, reactivation and/or other processes required for viral survival and infectivity, such virus or symptoms of such viruses can be treated or prevented using the compounds described herein, e.g., potent selective LSD1 inhibitors, LSD1/MAO-B dual inhibitors, cyclopropylamine acetamide derivatives, or cyclopropylamine derivatives. For example, recent studies showed that LSD1 interacts with HCF-1, and HCF-1 is required for the expression of the immediate early genes (IE), such as the IE genes of α-herpesviruses during the initiation of lytic infection. Depletion of LSD1 or inhibition of its activity with LSD1 or/and monoamine oxidase (MAO) inhibitors results in an increase in the levels of repressive histone H3-lysine 9 (H3K9) methylation, providing a central role for HCF-1 in modulating chromatin modifications that determine viral gene expression. A description of the role of LSD1 in lytic replication is set forth in Kristie et al. (*Nature Medicine* 15, 1312-1317 (2009)). Furthermore, the HCF-1 complex is also a crucial component of the reactivation mechanism and LSD1 or/and MAO inhibitors also block the reactivation of α-herpesviruses from latency. A description of the role of HCF-1 in reactivation from latency is set forth in Whitlow et al. (*J. Virol.*, 2009; Epub 0:JV1.01115-09v1).

Accordingly, in one embodiment, the present invention relates to a method of treating or preventing a viral infection of a host. The method of this embodiment comprises administering to the host an effective amount of a potent selective inhibitor of LSD 1 or a pharmaceutically acceptable salt thereof. In a more specific aspect, the method of this embodiment further comprises identifying a patient in need of such treatment or prevention.

In a related embodiment, the invention relates to a method of treating or preventing a reactivation of virus after latency. The method of this embodiment comprises administering to the host an effective amount of a potent selective inhibitor of LSD1 or a pharmaceutically acceptable salt thereof. In a more specific aspect, the method of this embodiment further comprises identifying a patient in need of such treatment or prevention.

As used herein, a potent LSD1 selective inhibitor refers to compounds that potently inhibits LSD1 activity, in particular compounds having a lower Ki value than the prior art compound Parnate. Preferably the potent selective LSD1 inhibitors have a Ki (IC50) value lower than 1 micromolar as determined by the assay described herein. More preferably, the potent selective inhibitor of LSD1 has a Ki value lower than 750 nanomolar. Even more preferably the potent selective inhibitor of LSD1 has a Ki value lower than 500 nanomolar. Preferably the potent LSD1 selective inhibitor is not a polypeptide, e.g., having three or peptide bonds linked together in a linear fashion as in a protein. As used herein, a polypeptide refers to a compound having more than three peptide bonds, preferably having more than five peptide bonds and even more preferably having more than 10 peptide bonds. The compounds of Example 1 are examples of LSD1/MAO-B dual inhibitors.

In one embodiment, the present invention provides a method of treating or preventing a viral infection of a host. The method according to this embodiment comprises administering to the host an effective amount of a LSD1/MAO-B dual inhibitor or a pharmaceutically acceptable salt thereof. In a more specific aspect, the method of this embodiment further comprises identifying a patient in need of such treatment or prevention.

In one embodiment, the present invention provides a method of treating or preventing reactivation of a virus after latency. The method according to this embodiment comprises administering to the host an effective amount of a LSD1/MAO-B dual inhibitor or a pharmaceutically acceptable salt thereof. In a more specific aspect, the method of this embodiment further comprises identifying a patient in need of such treatment or prevention.

As used herein, a LSD1/MAO-B dual inhibitor refers to compounds that inhibits LSD 1 and MAO-B to a greater extent than MAO-A. Preferably, the LSD1/MAO-B dual inhibitors have Ki (IC50) values for LSD1 and MAO-B which are at least two-fold lower than the Ki value for MAO-A as determined by the assays described herein. In a preferred aspect, the LSD1/MAO-B dual inhibitors have a Ki value for LSD1 and MAO-B which is at least five-fold lower than the Ki value for MAO-A. In an even more preferred aspect, the LSD1/MAO-B dual inhibitors have a Ki value for LSD1 and MAO-B which is at least ten-fold lower than the Ki value for MAO-A. The compounds of Example 2 are examples of LSD1/MAO-B dual inhibitors.

Cyclopropylamine acetamide derivative and cyclopropylamine derivatives compounds have been described as particularly potent inhibitors of LSD1 or LSD1/MAO-B. The novel use of cyclopropylamine acetamide derivatives and cyclopropylamine derivatives compounds can present a new method of treating or preventing infections caused by viruses.

As used herein, the term "cyclopropylamine acetamide derivative" refers to the compounds disclosed in patent applications EP 08166973.1 (filed Oct. 17, 2008), EP 09165840.1 (filed Jul. 17, 2009), PCT/EP2009/063685 (filed Oct. 19, 2009) and EP09172705.7 (filed Oct. 9, 2009) and which are herein expressly incorporated by reference in its entirety.

As used herein, the term "cyclopropylamine derivative" refers to the compounds disclosed in patent applications EP 09007970.7 (filed Jan. 21, 2009) PCT/EP2010/050697 (filed Jan. 21, 2010), EP 09171425.3 (filed Sep. 25, 2009), and EP 10150866.1 (filed Jan. 15, 2010), and which are herein expressly incorporated by reference in its entirety.

In one embodiment, the present invention provides a method of treating or preventing viral infection in a host. The method according to this embodiment comprises administering to the host an effective amount of a cyclopropylamine acetamide derivative or a pharmaceutically acceptable salt thereof. In a more specific aspect, the method of this embodiment further comprises identifying a patient in need of such treatment or prevention.

In one embodiment, the present invention relates to a method of treating or preventing viral infection in a host. The method according to this embodiment comprises administering to the host an effective amount of a cyclopropylamine derivative or a pharmaceutically acceptable salt thereof. In a more specific aspect, the method of this embodiment further comprises identifying a patient in need of such treatment or prevention.

In another embodiment, the present invention provides a method for preventing or treating reactivation of a virus after latency in a host. The method according to this embodiment comprises administering to the host an effective amount of a cyclopropylamine acetamide derivative or a pharmaceutically acceptable salt thereof. In a more specific aspect, the method of this embodiment further comprises identifying a patient in need of such treatment or prevention.

In another embodiment, the present invention provides a method for preventing or treating reactivation of a virus after latency in a host. The method of this embodiment comprises administering to the host an effective amount of a cyclopropylamine derivative or a pharmaceutically acceptable salt thereof. In a more specific aspect, the method of this embodiment further comprises identifying a patient in need of such treatment or prevention.

It is preferred that the host is a mammal and, more preferably, the host is a human.

Another embodiment of the present invention provides a method of preventing or treating a viral infection in a mammal that has undergone, is undergoing, or will undergo an organ or tissue transplant. The method according to this embodiment comprises administering to the mammal an effective amount of a potent selective LSD 1 inhibitor or a pharmaceutically acceptable salt thereof. A non-limiting example comprises administering an effective amount of a potent selective LSD1 inhibitor to a mammal receiving (or that has received) an organ or tissue known or suspected to be infected with virus.

Another embodiment of the present invention provides a method of preventing or treating a viral infection in a mammal that has undergone, is undergoing, or will undergo an organ or tissue transplant. The method of this embodiment comprises administering to the mammal an effective amount of a LSD1/MAO-B dual inhibitor or a pharmaceutically acceptable salt thereof. A non-limiting example comprises administering an effective amount of LSD1/MAO-B dual inhibitor to a mammal receiving (or that has received) an organ or tissue known or suspected to be infected with virus.

Another embodiment of the present invention provides a method of preventing or treating a viral infection in a mammal that has undergone, is undergoing, or will undergo an organ or tissue transplant. The method of this embodiment comprises administering to the mammal an effective amount of a cyclopropylamine acetamide derivative or a pharmaceutically acceptable salt thereof. A non-limiting example comprises administering an effective amount of a cyclopropylamine acetamide derivative compound to a mammal receiving (or that has received) an organ or tissue known or suspected to be infected with virus.

Another embodiment of the present invention provides a method of preventing or treating a viral infection in a mammal that has undergone, is undergoing, or will undergo an organ or tissue transplant. The method of this embodiment comprises administering to the mammal an effective amount of a cyclopropylamine derivative or a pharmaceutically acceptable salt thereof. A non-limiting example comprises administering an effective amount of a cyclopropylamine derivatives to a mammal receiving (or that has received) an organ or tissue known or suspected to be infected with virus.

In another aspect, the present invention provides the use of a potent selective LSD1 inhibitor for the treatment or prevention of the symptoms or effects of a viral infection in an infected host, which comprises treating said host with a therapeutically effective amount of a potent selective LSD1.

In another aspect, the present invention provides the use of a LSD1/MAO-B selective inhibitor for the treatment or prevention of the symptoms or effects of a viral infection in an infected host, which comprises treating said host with a therapeutically effective amount of a LSD1/MAO-B selective inhibitor.

In another aspect, the present invention provides the use of a cyclopropylamine acetamide derivative compound for the treatment or prevention of the symptoms or effects of a viral infection in an infected host, which comprises treating said host with a therapeutically effective amount of a compound according to the invention.

In another aspect, the present invention provides the use of a cyclopropylamine derivative compound for the treatment or prevention of the symptoms or effects of a viral infection in an infected host, which comprises treating said host with a therapeutically effective amount of a compound according to the invention.

Preferably, in the embodiments of the invention, the virus or a viral infection is one that depends on LSD1, protein complexes containing LSD1, gene expression dependent on LSD1 or LSD1 containing protein complexes, or signaling pathways related to LSD 1 activity.

In a preferred aspect, the virus or viral infection is selected from the group consisting of a herpes virus and an adenovirus.

In another preferred aspect, the virus or viral infection is a herpes virus selected from the group consisting of a herpes simplex virus type 1 (HSV-1), herpes simplex virus type 2 (HSV-2), varicella zoster virus (VZV), Epstein-Barr virus (EBV), cytomegalovirus (CMV), roseolovirus and rhadinovirus (including Kaposi's sarcoma-associated virus).

In a more preferred aspect, the virus or viral infection is selected from the group consisting of HSV-1 and HSV-2.

In another more preferred aspect, the virus or viral infection is EBV.

In another more preferred aspect, the virus or viral infection is VZV.

In one embodiment, the present invention relates to a method of treating or preventing viral infection in a host, comprising administering to the host an effective amount of a pharmaceutical composition comprising a potent selective LSD1 inhibitor and a pharmaceutical acceptable carrier. In one aspect of this embodiment, the pharmaceutical composition and pharmaceutically acceptable carrier is suitable for oral administration. In one aspect of this embodiment, the pharmaceutical composition and pharmaceutically acceptable carrier is suitable for topical administration.

In one embodiment, the present invention relates to a method of treating or preventing viral infection in a host, comprising administering to the host an effective amount of a pharmaceutical composition comprising a LSD1/MAO-B dual inhibitor and a pharmaceutical acceptable carrier. In one aspect of this embodiment, the pharmaceutical composition and pharmaceutically acceptable carrier is suitable for oral administration. In one aspect of this embodiment, the pharmaceutical composition and pharmaceutically acceptable carrier is suitable for topical administration.

In one embodiment, the present invention relates to a method of treating or preventing viral infection in a host, comprising administering to the host an effective amount of a pharmaceutical composition comprising a cyclopropylamine acetamide derivative and a pharmaceutical acceptable carrier. In one aspect of this embodiment, the pharmaceutical composition and pharmaceutically acceptable carrier is suitable for oral administration. In one aspect of this embodiment, the pharmaceutical composition and pharmaceutically acceptable carrier is suitable for topical administration.

In one embodiment, the present invention relates to a method of treating or preventing viral infection in a host, comprising administering to the host an effective amount of a pharmaceutical composition comprising a cyclopropylamine and a pharmaceutical acceptable carrier. In one aspect of this embodiment, the pharmaceutical composition and pharmaceutically acceptable carrier is suitable for oral administration. In one aspect of this embodiment, the pharmaceutical composition and pharmaceutically acceptable carrier is suitable for topical administration.

In one specific aspect, the present invention relates to a method of treating or preventing viral infection in a host. The method of this embodiment comprises topical administration to the host of an effective amount of a pharmaceutical composition comprising a potent selective LSD1 inhibitor or a LSD1/MAO-B dual inhibitor and a pharmaceutical acceptable carrier.

In one specific aspect, the present invention relates to a method of treating or preventing viral infection in a host. The method of this embodiment comprises topical administration to the host of an effective amount of a pharmaceutical composition comprising a cyclopropylamine acetamide derivative or a cyclopropylamine derivative and a pharmaceutical acceptable carrier.

In a more specific aspect, the present invention relates to a method of treating or preventing herpes virus in a host. The method of this embodiment comprises topical administration to the host of an effective amount of a pharmaceutical composition comprising a cyclopropylamine acetamide derivative or a cyclopropylamine derivative and a pharmaceutical acceptable carrier.

In one embodiment, the invention provides a method of treating HIV in an individual co-infected with a herpes simplex virus 2. According to this embodiment an individual having HIV and co-infected with herpes simplex virus 2 is administered a compound selected from a selective potent LSD 1 inhibitor, a dual LSD1/MAO-B inhibitor, a cyclopropylacetamide derivative, and a cyclopropylamine derivative, thereby treating HIV. In one aspect of this embodiment, the individual is administered one or more additional antiviral drugs wherein said one or more additional antiviral drugs is suitable for treating HIV. The anti HIV drug can be administered concomitantly or at different times (e.g., same or different times of the day or alternatively the HSV-2 infection can be suppressed first and then anti-HIV therapy can be initiated after suppression of the HSV-2 infection).

Specific examples of "cyclopropylamine acetamide" derivatives include, but are not limited to:

N-cyclopropyl-2-{[(trans)-2-phenylcyclopropyl]
    amino}acetamide;

2-{[(trans)-2-phenylcyclopropyl]amino}acetamide;

N-cyclopropyl-2-{[(trans)-2-phenylcyclopropyl]
    amino}propanamide;

2-{[(trans)-2-phenylcyclopropyl]amino}-N-prop-2-ynylacetamide;
N-isopropyl-2-{[(trans)-2-phenylcyclopropyl]amino}acetamide;
N-(tert-butyl)-2-{[(trans)-2-phenylcyclopropyl]amino}acetamide;
N-(2-morpholin-4-yl-2-oxoethyl)-N-[(trans)-2-phenylcyclopropyl]amine;
2-{[(trans)-2-phenylcyclopropyl]amino}propanamide;
Methyl 2-{[(trans)-2-phenylcyclopropyl]amino}propanoate;
1-(4-methylpiperazin-1-yl)-2-((trans)-2-phenylcyclopropylamino)ethanone;
1-(4-ethylpiperazin-1-yl)-2-((trans)-2-phenylcyclopropylamino)ethanone;
1-(4-benzylpiperazin-1-yl)-2-((trans)-2-phenylcyclopropylamino)ethanone;
2-((trans)-2-phenylcyclopropylamino)-1-(4-phenylpiperazin-1-yl)ethanone;
2-((trans)-2-(4-(benzyloxy)phenyl)cyclopropylamino)-1-(4-methylpiperazin-1-yl)ethanone;
2-((trans)-2-(1,1'-biphenyl-4-yl)cyclopropylamino)-1-(4-methylpiperazin-1-yl)ethanone;
2-((trans)-2-(4-(benzyloxy)phenyl)cyclopropylamino)-N-cyclopropylacetamide;
2-((trans)-2-(4-(3-fluorobenzyloxy)phenyl)cyclopropylamino)-1-(4-methyl piperazin-1-yl)ethanone;
2-((trans)-2-(4-(4-fluorobenzyloxy)phenyl)cyclopropylamino)-1-(4-methyl piperazin-1-yl)ethanone;
2-((trans)-2-(4-(3-chlorobenzyloxy)phenyl)cyclopropylamino)-1-(4-methyl piperazin-1-yl)ethanone;
1-(4-methylpiperazin-1-yl)-2-((trans)-2-(4-phenethoxyphenyl)cyclopropylamino)ethanone;
2-((trans)-2-(biphenyl-4-yl)cyclopropylamino)-1-(4-methylpiperazin-1-yl) ethanone; N-cyclopropyl-2-{[(trans)-2-phenylcyclopropyl]amino}acetamide;
N-methyl-trans-2-(Phenylcyclopropylamino)propanamide;
2-{methyl[(trans)-2-phenylcyclopropyl]amino}acetamide;
2-((trans)-2-(4-(4-cyanobenzyloxy)phenyl)cyclopropylamino)acetamide,
2-((trans)-2-(4-(3-cyanobenzyloxy)phenyl)cyclopropylamino)acetamide,
2-((trans)-2-(4-(benzyloxy)phenyl)cyclopropylamino)acetamide,
2-((trans)-2-(4-(4-fluorobenzyloxy)phenyl)cyclopropylamino)acetamide,
2-((trans)-2-(4-(3-fluorobenzyloxy)phenyl)cyclopropylamino)acetamide,
2-((trans)-2-(4-(3-chlorobenzyloxy)phenyl)cyclopropylamino)acetamide,
2-((trans)-2-(4-(4-chlorobenzyloxy)phenyl)cyclopropylamino)acetamide,
2-((trans)-2-(4-(3-bromobenzyloxy)phenyl)cyclopropylamino)acetamide,
2-((trans)-2-(4-(3,5-difluorobenzyloxy)phenyl)cyclopropylamino)acetamide,
2-((trans)-2-(4-phenethoxyphenyl)cyclopropylamino)acetamide,
2-((trans)-2-(3-(trifluoromethyl)biphenyl-4-yl)cyclopropylamino) acetamide,
2-((trans)-2-(3'-chlorobiphenyl-4-yl)cyclopropylamino)acetamide,
2-((trans)-2-phenylcyclopropylamino)-N-(piperidin-4-ylmethyl)acetamide;
N-(1-(dimethylamino)propan-2-yl)-2-((trans)-2-phenylcyclopropylamino)acetamide;
1-((S)-3-(dimethylamino)pyrrolidin-1-yl)-2-((trans)-2-phenylcyclopropylamino)ethanone;
1-((R)-3-(dimethylamino)pyrrolidin-1-yl)-2-((trans)-2-phenylcyclopropylamino)ethanone;
1-((S)-3-aminopyrrolidin-1-yl)-2-((trans)-2-phenylcyclopropylamino)ethanone;
2-((trans)-2-phenylcyclopropylamino)-N—((R)-pyrrolidin-3-yl)acetamide;
2-((trans)-2-phenylcyclopropylamino)-N—((R)-pyrrolidin-3-yl)acetamide;
2-((trans)-2-(4-(4-chlorobenzyloxy)phenyl)cyclopropylamino)-1-(4-methylpiperazin-1-yl)ethanone;
2-((trans)-2-(4-(3-bromobenzyloxy)phenyl)cyclopropylamino)-1-(4-methylpiperazin-1-yl)ethanone;
2-((4-((trans)-2-(2-(4-methylpiperazin-1-yl)-2-oxoethylamino)cyclopropyl)phenoxy)methyl)benzonitrile;
2-((trans)-2-(4-(biphenyl-4-ylmethoxy)phenyl)cyclopropylamino)-1-(4-methylpiperazin-1-yl)ethanone;
2-((trans)-2-(4-pyridin-3-ylphenyl) cyclopropylamino)-1-(4-methylpiperazin-1-yl)ethanone;
2-((trans)-2-(3'-methoxy-1,1'-biphenyl-4-yl)cyclopropylamino)-1-(4-methylpiperazin-1-yl)ethanone;
2-((trans)-2-(4-methoxybiphenyl-4-yl)cyclopropylamino)-1-(4-methylpiperazin-1-yl)ethanone;
4'-((trans)-2-(2-(4-methylpiperazin-1-yl)-2-oxoethylamino)cyclopropyl)biphenyl-3-carbonitrile;
4'-((trans)-2-(2-(4-methylpiperazin-1-yl)-2-oxoethylamino)cyclopropyl)biphenyl-4-carbonitrile;
2-((trans)-2-(4-fluorobiphenyl-4-yl)cyclopropylamino)-1-(4-methylpiperazin-1-yl)ethanone;
1-(4-methylpiperazin-1-yl)-2-((trans)-2-(3'-(trifluoromethyl)biphenyl-4-yl)cyclopropylamino)ethanone;
1-(4-methylpiperazin-1-yl)-2-((trans)-2-(4'-(methylsulfonyl)biphenyl-4-yl)cyclopropylamino)ethanone;
2-((trans)-2-(3',5'-dichlorobiphenyl-4-yl)cyclopropylamino)-1-(4-methylpiperazin-1-yl)ethanone;
2-((trans)-2-(2',4-difluorobiphenyl-4-yl)cyclopropylamino)-1-(4-methylpiperazin-1-yl)ethanone;
2-((trans)-2-(4-(6-methoxypyridin-3-yl)phenyl)cyclopropylamino)-1-(4-methylpiperazin-1-yl)ethanone;
2-((trans)-2-(2'-fluorobiphenyl-4-yl)cyclopropylamino)-1-(4-methylpiperazin-1-yl)ethanone;
2-(4-methylpiperazin-1-yl)-2-((trans)-2-(4'-(trifluoromethyl)biphenyl-4-yl)cyclopropylamino)ethanone;
1-(4-methylpiperazin-1-yl)-2-((trans)-2-(2'-(trifluoromethyl)biphenyl-4-yl)cyclopropylamino)ethanone;
1-(4-methylpiperazin-1-yl)-2-((trans)-2-(4'-(trifluoromethoxy)biphenyl-4-yl)cyclopropylamino)ethanone;
2-((trans)-2-(3'-fluorobiphenyl-4-yl)cyclopropylamino)-1-(4-methylpiperazin-1-yl)ethanone;
2-((trans)-2-(4-fluoro-2'-methoxybiphenyl-4-yl)cyclopropylamino)-1-(4-methylpiperazin-1-yl)ethanone;
1-(4-methylpiperazin-1-yl)-2-((trans)-2-(4-(pyridin-4-yl)phenyl)cyclopropylamino)ethanone;
2-((trans)-2-(3'-chlorobiphenyl-4-yl)cyclopropylamino)-1-(4-methylpiperazin-1-yl)ethanone;
2-((trans)-2-(4'-chlorobiphenyl-4-yl)cyclopropylamino)-1-(4-methylpiperazin-1-yl)ethanone;
2-((trans)-2-(5'-fluoro-2'-(trifluoromethyl)biphenyl-4-yl)cyclopropylamino)-1-(4-methylpiperazin-1-yl)ethanone;
2-((trans)-2-(4-(2-methoxypyridin-3-yl)phenyl)cyclopropylamino)-1-(4-methylpiperazin-1-yl)ethanone;
1-(4-methylpiperazin-1-yl)-2-((trans)-2-(4-phenethylphenyl)cyclopropylamino)ethanone; and
2-((trans)-2-(4-cyclopropylphenyl)cyclopropylamino)-1-(4-methylpiperazin-1-yl)ethanone.

Specific examples of "cyclopropylamine" derivatives, include, but are not limited to:

N-4 fluorobenzyl-N-{(trans)-2-[4-(benzyloxy)phenyl]cyclopropyl}amine,
N-4-methoxybenzyl-N-{(trans)-2-[4-(benzyloxy)phenyl]cyclopropyl}amine,
N-benzyl-N-{(trans)-2-[4-(benzyloxy)phenyl]cyclopropyl}amine,
N-[(trans)-2-phenylcyclopropyl]amino-methyl)pyridin-3-ol,
N-[(trans)-2-phenylcyclopropyl]-N-(3-methyl-pyridin-2-yl-methyl)amine,
N-[(trans)-2-phenylcyclopropyl]-N-(4-chloropyridin-3-yl-methyl)amine,
N-[(trans)-2-phenylcyclopropyl]-N-(4-trifluoromethylpyridin-3-yl-methyl)amine,
N-(3-methoxybenzyl)-N-[(trans)-2-phenylcyclopropyl]amine,
N-[(trans)-2-phenylcyclopropyl]-N-(quinolin-4-ylmethyl)amine,
N-(2-fluorobenzyl)-N-[(trans)-2-phenylcyclopropyl]amine,
N-(3-fluorobenzyl)-N-[(trans)-2-phenylcyclopropyl]amine,
N-[(trans)-2-phenylcyclopropyl]-N-(3,4-dichloro-1-phenyl-methyl)amine,
N-[(trans)-2-phenylcyclopropyl]-N-(5-bromo-thiophen-2-ylmethyl)amine,
N-[(trans)-2-phenylcyclopropyl]-N-(3-bromo-thiophen-2-ylmethyl)amine,
N-[(trans)-2-phenylcyclopropyl]-N-(thiophen-2-ylmethyl)amine,
N-[(trans)-2-phenylcyclopropyl]-N-(1,3-thiazol-2-ylmethyl)amine,
N-[(trans)-2-phenylcyclopropyl]-N-(3-methyl-pyridin-2-yl-methyl)amine,
N-[(trans)-2-phenylcyclopropyl]-N-(pyridin-4-ylmethyl)amine,
N-[(trans)-2-phenylcyclopropyl]-N-(pyridin-3-ylmethyl)amine,
N-[(trans)-2-phenylcyclopropyl]-N-(pyridin-2-ylmethyl)amine,
[(trans)-2-phenylcyclopropyl]-N-[4-(trifluoromethyl)benzyl]amine,
({[(trans)-2-phenylcyclopropyl]amino}methyl)benzonitrile,
N-(4-fluorobenzyl)-N-[(trans)-2-phenylcyclopropyl]amine,
N-[(trans)-2-phenylcyclopropyl]-N-(3-bromo-pyridin-2-yl-methyl)amine,
N-cyanobenzyl-N-{(trans)-2-[4-(benzyloxy)phenyl]cyclopropyl}amine,
N-4-[(benzyloxy)-benzyl]-N-[(trans)-2-(4-phenyl)cyclopropyl]amine;
N-[2-(4-methylpiperazin-1-yl)ethyl]-N-[(trans)-2-phenylcyclopropyl]amine;
N-cyclopropyl-N'-[(trans)-2-phenylcyclopropyl]ethane-1,2-diamine;
N,N-dimethy-N'-(2-{[(trans)-2-phenylcyiopropyl]amino}ethyl)ethane-1,2-diamine;
(3R)-1-(2-{[trans-2-phenylcyclopropyl]amino}ethyl)pyrrolidin-3-amine;
(3S)—N,N-dimethyl-1-(2-{[(trans)-2-phenylcyclopropyl]amino}ethyl) pyrrolidin-3-amine;
(3R)—N,N-dimethyl-1-(2-{[(trans)-2-phenylcyclopropyl]amino}ethyl) pyrrolidin-3-amine;
N-[(trans)-2-phenylcyclopropyl]-N-(2-piperazin-1-ylethyl)amine;
N,N-diethyl-N'-[(trans)-2-phenylcyclopropyl]ethane-1,2-diamine;
N-[(trans)-2-phenylcyclopropyl]-N-(2-piperidin-1-ylethyl)amine;
(trans)-2-(4-(benzyloxy)phenyl)-N-(2-(4-methylpiperazin-1-yl)ethyl)cyclopropanamine;
(trans)-N-(2-(4-methylpiperazin-1-yl)ethyl)-2-(3'-(trifluoromethyl) biphenyl-4-yl)cyclopropanamine;
(trans)-2-(3'-chlorobiphenyl-4-yl)-N-(2-(4-methylpiperazin-1-yl)ethyl)cyclopropanamine;
(R)-1-(2-((trans)-2-(3'-(trifluoromethyl)biphenyl-4-yl)cyclopropylamino)
ethyl)pyrrolidin-3-amine;
$N^1$-cyclopropyl-$N^2$-((trans-2-(3'-(trifluoromethyl)biphenyl-4-yl)cyclopropyl)ethane-1,2-diamine;
(trans)-N-((6-methylpyridin-2-yl)methyl)-2-phenylcyclopropanamine;
(trans)-N-((4-bromothiophen-2-yl)methyl)-2-phenylcyclopropanamine;
(trans)-2-phenyl-N-((6-(trifluoromethyl)pyridin-3-yl) methyl)cyclopropanamine;
(trans)-N-((6-chloropyridin-3-yl)methyl)-2-phenylcyclopropanamine;
(trans)-N-((4-methylpyridin-2-yl)methyl)-2-phenylcyclopropanamine;
(trans)-N-((6-methoxypyridin-2-yl)methyl)-2-phenylcyclopropanamine;
(trans)-N-((6-bromopyridin-2-yl)methyl)-2-phenylcyclopropanamine;
(trans)-2-phenyl-N-(quinolin-2-ylmethyl)cyclopropanamine;
(trans)-2-phenyl-N-((5-(trifluoromethyl)pyridin-2-yl) methyl)cyclopropanamine;
(trans)-N-((3-fluoropyridin-2-yl)methyl)-2-phenylcyclopropanamine;
(trans)-2-phenyl-N-(quinolin-3-ylmethyl)cyclopropanamine;
(trans)-N-((6-methoxypyridin-3-yl)methyl)-2-phenylcyclopropanamine;
(trans)-N-((5-methoxypyridin-3-yl)methyl)-2-phenylcyclopropanamine;
(trans)-N-((2-methoxypyridin-3-yl)methyl)-2-phenylcyclopropanamine;
(trans)-N-((3H-indol-3-yl)methyl)-2-phenylcyclopropanamine;
3-(((trans)-2-phenylcyclopropylamino)methyl)benzonitrile;
(trans)-N-(2-methoxybenzyl)-2-phenylcyclopropanamine;
3-(((trans)-2-phenylcyclopropylamino)methyl)pyridin-2-amine;
(trans)-N-((2-chloropyridin-3-yl)methyl)-2-phenylcyclopropanamine;
(trans)-N-(3,4-dimethoxybenzyl)-2-phenylcyclopropanamine;
(trans)-N-((2,3-dihydrobenzofuran-5-yl)methyl)-2-phenylcyclopropanamine;
(trans)-N-(benzo[d][1,3]dioxol-5-ylmethyl)-2-phenylcyclopropanamine;
(trans)-N-((2,3-dihydrobenzo[b][1,4]dioxin-8-yl)methyl)-2-phenylcyclopropanamine;
(trans)-N-(2,6-difluoro-4-methoxybenzyl)-2-phenylcyclopropanamine;
(trans)-2-phenyl-N-(4-(trifluoromethoxy)benzyl)cyclopropanamine;
(trans)-N-(5-fluoro-2-methoxybenzyl-2-phenylcyclopropanamine;
(trans)-N-(2-fluoro-4-methoxybenzyl)-2-phenylcyclopropanamine;
(trans)-N-((4-methoxynaphthalen-1-yl)methyl)-2-phenylcyclopropanamine;

(trans)-N-(2-fluoro-6-methoxybenzyl)-2-phenylcyclopropanamine;
(trans)-N-((2-methoxynaphthalen-1-yl)methyl)-2-phenylcyclopropanamine;
(trans)-N-((4,7-dimethoxynaphthalen-1-yl)methyl)-2-phenylcyclopropanamine;
(trans)-N-(4-methoxy-3-methylbenzyl)-2-phenylcyclopropanamine;
(trans)-N-(3-chloro-4-methoxybenzyl)-2-phenylcyclopropanamine;
(trans)-N-(3-fluoro-4-methoxybenzyl)-2-phenylcyclopropanamine;
(trans)-N-(4-methoxy-2-methylbenzyl)-2-phenylcyclopropanamine;
(trans)-N-((3,4-dihydro-2H-benzo[b][1,4]dioxepin-6-yl)methyl)-2-phenylcyclopropanamine;
(trans)-N-((3,4-dihydro-2H-benzo[b][1,4]dioxepin-7-yl)methyl)-2-phenylcyclopropanamine;
(trans)-N-((2,2-dimethylchroman-6-yl)methyl)-2-phenylcyclopropanamine;
(trans)-N-(4-methoxy-2,3-dimethylbenzyl)-2-phenylcyclopropanamine;
(trans)-N-(4-methoxy-2,5-dimethylbenzyl)-2-phenylcyclopropanamine;
(trans)-N-(2-fluoro-4,5-dimethoxybenzyl)-2-phenylcyclopropanamine;
(trans)-N-(3-chloro-4,5-dimethoxybenzyl)-2-phenylcyclopropanamine;
(trans)-N-(2-chloro-3,4-dimethoxybenzyl)-2-phenylcyclopropanamine;
(trans)-N-(2,4-dimethoxy-6-methylbenzyl)-2-phenylcyclopropanamine;
(trans)-N-(2,5-dimethoxybenzyl)-2-phenylcyclopropanamine;
(trans)-N-(2,3-dimethoxybenzyl)-2-phenylcyclopropanamine;
(trans)-N-(2-chloro-3-methoxybenzyl)-2-phenylcyclopropanamine;
(trans)-N-((1H-indol-5-yl)methyl)-2-phenylcyclopropanamine;
(trans)-2-(4-(benzyloxy)phenyl)-N-(pyridin-2-ylmethyl)cyclopropanamine;
(trans-2-(4-(benzyloxy)phenyl)-N-(2-methoxybenzyl)cyclopropanamine;
(trans)-N-(1-(3,4-dimethoxyphenyl)ethyl)-2-phenylcyclopropanamine;
(trans)-N-(1-(2,3-dihydrobenzo[b][1,4]dioxin-6-yl)ethyl)-2-phenylcyclopropanamine;
(trans)-N-(1-(5-fluoro-2-methoxyphenyl)ethyl)-2-phenylcyclopropanamine;
(trans)-N-(1-(3,4-dimethoxyphenyl)propan-2-yl)-2-phenylcyclopropanamine;
(trans)-N-((3-methyl-1,2,4-oxadiazol-5-yl)methyl)-2-phenylcyclopropanamine;
N-(trans)-2-(isobutylthio)-ethyl-2-phenylcyclopropanamine;
N-trans-(2-ethoxyethyl)-2-phenylcyclopropanamine;
N-trans-(2-methoxyethyl)-2-phenylcyclopropanamine;
N1-((trans)-2-(4-(3-bromobenzyloxy)phenyl)cyclopropyl)-N2-cyclopropylethane-1,2-diamine;
N1-((trans)-2-(3'-chlorobiphenyl-4-yl)cyclopropyl)-N2-cyclopropylethane-1,2-diamine;
N1-cyclopropyl-N2-((trans)-2-(4-phenethoxyphenyl)cyclopropyl)ethane-1,2-diamine;
N1,N1-diethyl-N2-((trans)-2-(4-(3 fluorobenzyloxy)phenyl)cyclopropyl)ethane-1,2-diamine;
(trans)-2-(4-bromophenyl)-N-(2-(4-methylpiperazin-1-yl)ethyl)cyclopropanamine;
(trans)-N-(2-(piperidin-1-yl)ethyl)-2-(3'-(trifluoromethyl)biphenyl-4-yl)cyclopropanamine;
N1,N1-diethyl-N2-((trans)-2-(3'-(trifluoromethyl)biphenyl-4-yl)cyclopropyl)ethane-1,2-diamine;
(trans)-N-(2-(piperazin-1-yl)ethyl)-2-(3'-(trifluoromethyl)biphenyl-4-yl)cyclopropanamine;
(S)-1-(2-((trans)-2-(3'-(trifluoromethyl)biphenyl-4-yl)cyclopropylamino)ethyl)pyrrolidin-3-amine;
(R)-1-(2-((trans)-2-(3'-chlorobiphenyl-4-yl)cyclopropylamino)ethyl)pyrrolidin-3-amine;
(R)-1-(2-((trans)-2-(4'-chlorobiphenyl-4-yl)cyclopropylamino)ethyl)pyrrolidin-3-amine;
(R)-1-(2-((trans)-2-(3'-methoxybiphenyl-4-yl)cyclopropylamino)ethyl)pyrrolidin-3-amine;
(R)-1-(2-((trans)-2-(4-(3-bromobenzyloxy)phenyl)cyclopropylamino)ethyl)pyrrolidin-3-amine; and
(R)-1-(2-((trans)-2-(6-(3-(trifluoromethyl)phenyl)pyridin-3-yl)cyclopropylamino)ethyl)pyrrolidin-3-amine.

Combination Treatments

The compounds of the invention, e.g., selective potent LSD1 inhibitors, LSD11/MAO-B dual inhibitors, cyclopropylamineacetamide derivatives and cyclopropylamine derivatives, can be administered in combination with other pharmaceutical agents, preferably antiviral agents. Administered in combination means that the different pharmaceutical agents are administered to the same patient. The pharmaceutical agents can be administered at the same time (e.g., twice daily) or different times (one agent in the morning the other agent in the evening). The pharmaceutical agents can be administered by the same (e.g., oral) or different routes of administration (e.g., oral and topical).

In one embodiment, the present invention relates to a method of treating or preventing viral infection in a host comprising administering to the host an effective amount of first agent which is a potent selective LSD1 inhibitor or a LSD1/MAO-B inhibitor in combination with a second agent or agents which are one or more antiviral agents. In one aspect of this embodiment the one or more antiviral agents are selected from the group consisting of acyclovir, famciclovir, ganciclovir, foscarnet, cidofovir, fomivirsen, AZT, ddl, ddC, 3TC, and d4T. In one aspect, the antiviral agent is chosen from acyclovir and famciclovir. In one aspect, the first agent is a potent selective LSD1 inhibitor. In one aspect, the first agent is a LSD1/MAO-B dual inhibitor.

In one embodiment, the present invention relates to a method of treating or preventing viral infection in a host comprising administering to the host an effective amount of a first agent which is a cyclopropylamine acetamide derivative or a cyclopropylamine derivative in combination with a second agent which is one or more antiviral agents. In one aspect of this embodiment the one or more antiviral agents are selected from the group consisting of acyclovir, famciclovir, penciclovir, ganciclovir, foscarnet, cidofovir, fomivirsen, AZT, ddl, ddC, 3TC, d4T, and pharmaceutically acceptable derivatives and mixtures thereof. In one aspect, the antiviral agent is chosen from acyclovir and famciclovir. In one aspect, the first agent is a cyclopropylacetamide derivative. In one aspect, the first agent is a cyclopropylamine derivative.

Antiviral and anti-HIV drugs include the non-nucleoside reverse transcriptase inhibitors (e.g., etravine, efavirenz, delavirdine, nevirapene), the nucleoside/nucleotide reverse transcriptase inhibitors (e.g., AZT, lamivudine, emtricitabine, didanosine, tenofovir disoproxil, abacavir, stavudine), the protease inhibitors (e.g., tipranavir, ritonavir, indinavir, daruavir, saquinavir, atazanavir, lopinavir, nelfinavir, fosamprenavir), the CCR antagonists (e.g., maraviroc), fusion inhibitors (e.g., enfuvirtide), integrase inhibitors (e.g., raltegravir) and fixed dose combinations of these types of drugs.

Route of Administration, Formulations and Dosages

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Topical administration refers to administration to skin or a mucous membrane. Routes of topical administration include skin, nasal, buccal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by cross-linking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al. (1984) *J. Pharmaceut. Sci.*, 73: 1718-1720.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

Prodrugs

The active compounds can also be conjugated, to a water soluble non-immunogenic non-peptidic high molecular weight polymer to form a polymer conjugate.

For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) *Am. J. Hosp. Pharm.* 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

DEFINITIONS

As used herein, a "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, and mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

The term "therapeutic effective amount" or "therapeutically effective amount" is used throughout the specification to describe concentrations or amounts of compounds according to the present invention which are therapeutically effective in treating or preventing viruses according to the present invention.

The term "effective amount" shall mean an amount or concentration of a compound according to the present invention which is effective within the context of its administration or use, including, for example, the treatment or prevention of viral infections.

A "host" may be considered a single cell, a tissue, an organ, or an individual organism, such as a mammal. The mammal can be any mammal, such as a mammal selected from the group consisting of a mouse, rat, guinea pig, hamster, cat, dog, pig, cow, horse, and primate. In one embodiment, the mammal is a human.

A "viral infection" is present in a host when a virus replicates itself within the host. A virus contains its own genetic material but uses the machinery of the host to reproduce. The virus may reproduce immediately, whereby the resulting virions destroy a host cell to attack additional cells. This process is the viral lytic cycle. Alternatively, a virus may establish a quiescent infection in a host cell, lying dormant until environmental stimuli trigger re-entry into the lytic replication cycle. Such re-emergence or re-entry into the lytic replication cycle is termed re-activation.

As used herein, Ki (IC50) values of the present inhibitors were estimated at half of the maximum activity according to their ability to inhibit LSD 1 and MAOs in the biological assays as describe herein in the examples below.

EXAMPLES

Example 1

Specific examples of potent selective inhibitors of LSD1 are, without limitation:

Compound 1(A)

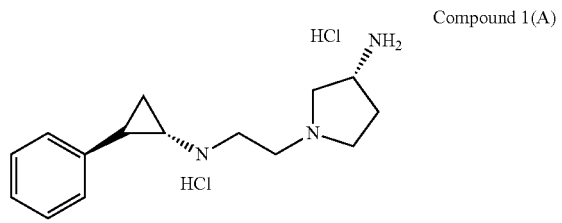

-continued

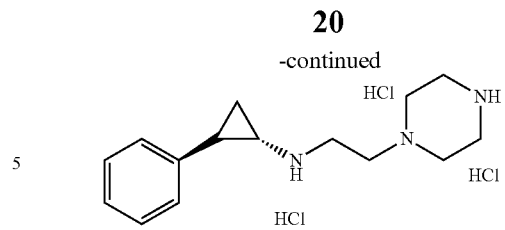

These examples (1(A) and 1(B)) are potent LSD1 selective inhibitors, the compounds have Ki (IC50) values lower than 1 micromolar. For example, compound 1(A) has a Ki value for LSD1 of between 1 to 100 nanomolar and for MAO-A and MAO-B of greater than 40 micromolar, compound 1(B) has an Ki value for LSD1 of between 1 to 100 nanomolar and for MAO-A and MAO-B of greater than 30 micromolar. Thus the Ki values for these potent selective LSD1 inhibitors are more than 50-fold lower than the Ki values for MAO-B and MAO-A.

Example 2

Specific examples of dual LSD1/MAO-B selective inhibitors are, without limitation:

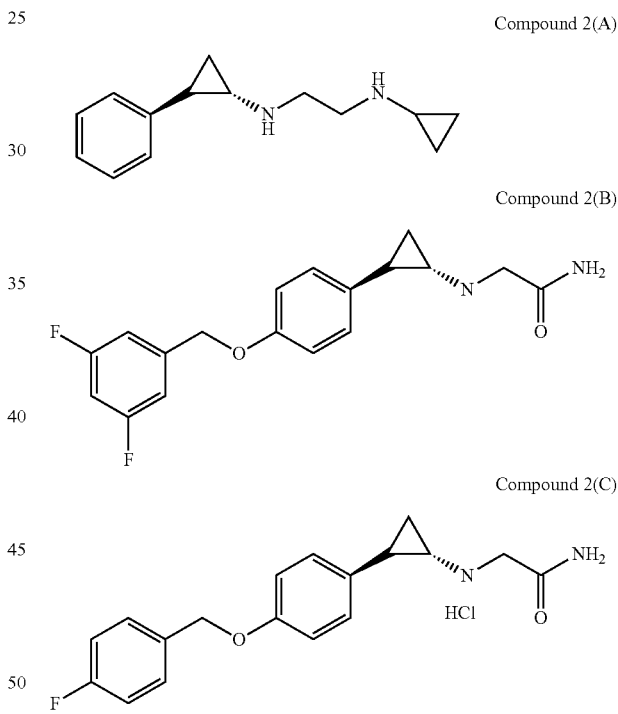

These LSD1/MAO-B dual inhibitors have Ki values for LSD1/MAO-B about at least 10-fold lower than the Ki values for MAO-A. Compound 2(A) has a Ki value for MAO-A of about 10 micromolar and the Ki values for MAO-B and LSD1 are at least 10-20 fold lower, compound 2(B) has an Ki value for MAO-A of between 20 to 30 micromolar and the Ki values for MAO-B and LSD1 are at least 10-20 fold lower, Compound 2(C) has an Ki value for MAO-A of greater than 40 micromolar and the Ki values for MAO-B and LSD1 at least 100 fold lower.

Example 3

To evaluate the compounds of the present invention against HSV-1 and HSV-2 viruses, anti-HSV drug screening assay can be used for the primary analysis of compounds.

The basic assay involves infection of Vero cells with HSV-1 or HSV-2 in the presence of the compounds of the invention (e.g., selective potent LSD inhibitors, dual LSD1/MAO-B inhibitors, cyclopropylamine acetamide derivatives, or cyclopropylamine derivatives) and appropriate controls. The ability of the compounds to inhibit HSV-induced cell killing is measured five days post-infection using the tetrazolium dye MTS (Cell Titer 96 Aqueous One Solution, Promega). Mitochondrial enzymes of viable (surviving) cells convert MTS to a soluble, colored formazan product. Quantitation of the amount of the formazan product present in each well of the microtiter plate is determined spectrophotometrically at 490/650 nm. The toxicity of the test compounds to host cells can be measured concurrently in the same microtiter plate. Data can be analyzed using a statistical software program along with determinations of the efficacy (IC50), toxicity (TC50) and selectivity (therapeutic index, TI) of the compounds. Standard Syncytia/Plaque Reduction assays can be also suitable.

Example 4

Repression of varicella zoster virus expression by compounds of the invention (e.g., selective potent LSD inhibitors, dual LSD1/MAO-B inhibitors, cyclopropylamine acetamide derivatives, or cyclopropylamine derivatives) can be examined by a standard plaque-reduction assay as is known to the skilled artisan see e.g., Erazo et al. (2008) (*J. Virol.* 82:7653-7665) or Taylor et al. (2004) (*J. Virol.* 78:2853-2862).

Example 5

Repression of Epstein-Barr virus (EBV) expression by compounds of the invention (e.g., selective potent LSD inhibitors, dual LSD1/MAO-B inhibitors, cyclopropylamine acetamide derivatives, or cyclopropylamine derivatives) can be done following the standard art-known procedures to identify inhibitors of EBV. One example of such an assay is a PCR-based assay. This assay is performed using P3HR1 cells, a cell line that is latently infected with EBV. Lytic virus replication spontaneously occurs in approximately 5% of the cell population resulting in the release of virus particles from the cells. P3HR1 cells are incubated with compounds for a period of six days. Supernatant virus is collected and quantitated using TaqMan (PE Applied Biosystems) PCR methodology. Compound toxicity is evaluated in parallel using MTS.

Example 6

Inhibition of the α-Herpesvirus Re-Activation Cycle by Compounds of the Invention Methods known to the skilled artisan can be used to test for inhibition of the α-herpesvirus re-activation cycle by compounds of the invention. Latently infected mice and trigeminal ganglia: Balb/c mice can be infected with 5×10$^5$ PFU HSV-I per eye after corneal scarification. Latently infected mice are sacrificed 30 days post clearance of the primary infection and trigeminal ganglia is rapidly explanted into culture in the presence or absence of a compound of the invention (e.g., selective potent LSD inhibitors, dual LSD1/MAO-B inhibitors, cyclopropylamine acetamide derivatives, or cyclopropylamine derivatives) or control (DMSO or acyclovir). Post explant incubation, the ganglia is homogenized and briefly sonicated. The reactivated viral yield of each ganglia can be determined by titering the clarified supernatant on Vero cells.

Example 7

Repression of adenovirus (E1A) expression by compounds of the invention (e.g., selective potent LSD inhibitors, dual LSD1/MAO-B inhibitors, cyclopropylamine acetamide derivatives, or cyclopropylamine derivatives) can be demonstrated following the standard procedure of viral infection and treatment with a compound of the invention: HeLa cells are treated with control DMSO or compounds of the invention for 5 hours prior to infection with various amounts of Adenovirus Type 5 for 2-4 hours. Equal amounts of infected cell lysates are resolved by SDS-PAGE and Western blotted with anti-E1 A, anti-LSD 1, and anti-β. tubulin antibodies. HEK293 and uninfected HeLa cell lysates represent E1A positive and negative controls.

Example 8

Dose-dependent repression of adenovirus E1A expression by a compound of the invention (e.g., selective potent LSD inhibitors, dual LSD1/MAO-B inhibitors, cyclopropylamine acetamide derivatives, or cyclopropylamine derivatives) can be demonstrated with methods known to the skilled artisan. For example by treating HeLa cells with control DMSO or various concentrations of a compound of the invention for 5 hours prior to infection with adenovirus Type 5 for 2 hours. Equal amounts of infected cell lysates are resolved by SDS-PAGE and Western blotted with anti-E1 A, anti-β Tubulin, and anti-TBP antibodies.

Example 9

Biological Assays

The compounds of the invention can be tested for their ability to inhibit LSD1. The ability of compounds inhibit LSD1 can be tested as follows. Human recombinant LSD1 protein was purchased from BPS Bioscience Inc. In order to monitor LSD1 enzymatic activity and/or its inhibition rate by our inhibitor(s) of interest, di-methylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen).

Briefly, a fixed amount of LSD 1 was incubated on ice for 15 minutes, in the absence and/or in the presence of various concentrations of inhibitor (e.g., from 0 to 75 μM, depending on the inhibitor strength). Tranylcypromine (Biomol. International) was used as a control for inhibition. Within the experiment, each concentration of inhibitor was tested in triplicate. After leaving the enzyme interacting with the inhibitor, 12.5 μM of di-methylated H3-K4 peptide was add to each reaction and the experiment was left for 1 hour at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and leaved to incubate for 30 extra minutes at room temperature in the dark. A 1 μM $H_2O_2$ solution was used as a control of the kit efficiency. The conversion of the Amplex®. Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD 1 was obtained in the absence of inhibitor and corrected for background fluorescence in the absence of LSD1. The Ki of each inhibitor was estimated at half of the maximum activity.

Parnate (2-trans phenylcyclopropylamine) was found to have a Ki of from about 15 to 35 micromolar depending on the enzyme preparation. The studies show that the compounds of the invention have unexpectedly potent LSD1 inhibition.

Example 10

Biological Assays-Monoamine Oxidase Assays for Determining the Selectivity of the Compounds of the Invention for LSD1

Human recombinant monoamine oxidase proteins MAO-A and MAO-B were purchased from Sigma Aldrich. MOAs catalyze the oxidative deamination of 1°, 2' and 3° amines. In order to monitor MAO enzymatic activities and/or their inhibition rate by inhibitor(s) of interest, a fluorescent-based (inhibitor)-screening assay was set up. 3-(2-Aminophenyl)-3-oxopropamamine (kynuramine dihydrobromide, Sigma Aldrich), a non fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µL. The assay buffer was 100 mM HEPES, pH 7.5. Each experiment was performed in triplicate within the same experiment.

Briefly, a fixed amount of MAO (0.25. µg for MAO-A and 0.5 µg for MAO-B) was incubated on ice for 15 minutes in the reaction buffer, in the absence and/or in the presence of various concentrations of inhibitor (e.g., from 0 to 50 µM, depending on the inhibitor strength). Tranylcypromine (Biomol. International) was used as a control for inhibition.

After leaving the enzyme(s) interacting with the inhibitor, 60 to 90 µM of kynuramine was added to each reaction for MAO-B and MAO-A assay respectively, and the reaction was left for 1 hour at 37° C. in the dark. The oxidative deamination of the substrate was stopped by adding 50 µL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki of each inhibitor was measure at Vmax/2.

What is claimed is:

1. A method of treating a viral infection selected from a herpesvirus or adenovirus in a mammal, the method comprising administering to said mammal a therapeutically effective amount of a potent selective LSD1 (lysine-specific demethylase-1) inhibitor or a LSD1/MAO-B (monoamine oxidase-B) dual inhibitor, or a pharmaceutically acceptable salt thereof, wherein the potent selective LSD1 inhibitor or LSD1/MAO-B dual inhibitor is a cyclopropylamine acetamide derivative or a cyclopropylamine derivative selected from the group consisting of:
   N-cyclopropyl-2-{[(trans)-2-phenylcyclopropyl]amino}acetamide;
   2-{[(trans)-2-phenylcyclopropyl]amino}acetamide;
   N-cyclopropyl-2-{[(trans)-2-phenylcyclopropyl]amino}propanamide;
   2-{[(trans)-2-phenylcyclopropyl]amino}-N-prop-2-ynylacetamide;
   N-(2-morpholin-4-yl-2-oxoethyl)-N-[(trans)-2-phenylcyclopropyl]amine;
   2-{[(trans)-2-phenylcyclopropyl]amino}propanamide;
   Methyl 2-{[(trans)-2-phenylcyclopropyl]amino}propanoate;
   1-(4-methylpiperazin-1-yl)-2-((trans)-2-phenylcyclopropylamino)ethanone;
   1-(4-ethylpiperazin-1-yl)-2-((trans)-2-phenylcyclopropylamino)ethanone;
   1-(4-benzylpiperazin-1-yl)-2-((trans)-2-phenylcyclopropylamino)ethanone;
   2-((trans)-2-phenylcyclopropylamino)-1-(4-phenylpiperazin-1-yl)ethanone;
   2-((trans)-2-(4-(benzyloxy)phenyl)cyclopropylamino)-1-(4-methylpiperazin-1-yl)ethanone;
   2-((trans)-2-(1,1'-biphenyl-4-yl)cyclopropylamino)-1-(4-methylpiperazin-1-yl)ethanone;
   2-((trans)-2-(4-(benzyloxy)phenyl)cyclopropylamino)-N-cyclopropylacetamide;
   2-((trans)-2-(4-(3-fluorobenzyloxy)phenyl)cyclopropylamino)-1-(4-methylpiperazin-1-yl)ethanone;
   2-((trans)-2-(4-(4-fluorobenzyloxy)phenyl)cyclopropylamino)-1-(4-methylpiperazin-1-yl)ethanone;
   2-((trans)-2-(4-(3-chlorobenzyloxy)phenyl)cyclopropylamino)-1-(4-methylpiperazin-1-yl)ethanone;
   1-(4-methylpiperazin-1-yl)-2-((trans)-2-(4-phenethoxyphenyl) cyclopropylamino)ethanone;
   2-((trans)-2-(biphenyl-4-yl)cyclopropylamino)-1-(4-methylpiperazin-1-yl)ethanone;
   N-[2-(4-methylpiperazin-1-yl)ethyl]-N-[(trans)-2-phenylcyclopropyl]amine;
   N-cyclopropyl-N'-[(trans)-2-phenylcyclopropyl]ethane-1,2-diamine;
   N,N-dimethyl-N'-(2-{[(trans)-2-phenylcyclopropyl]amino}ethyl)ethane-1,2-diamine;
   (3R)-1-(2-{[(trans)-2-phenylcyclopropyl]amino}ethyl)pyrrolidin-3-amine;
   (3S)—N,N-dimethyl-1-(2-{[(trans)-2-phenylcyclopropyl]amino}ethyl)pyrrolidin-3-amine;
   (3R)—N,N-dimethyl-1-(2-{[(trans)-2-phenylcyclopropyl]amino}ethyl)pyrrolidin-3-amine;
   N-[(trans)-2-phenylcyclopropyl]-N-(2-piperazin-1-ylethyl)amine;
   N,N-diethyl-N'-[(trans)-2-phenylcyclopropyl]ethane-1,2-diamine;
   N-[(trans)-2-phenylcyclopropyl]-N-(2-piperidin-1-ylethyl)amine;
   (trans)-2-(4-(benzyloxy)phenyl)-N-(2-(4-methylpiperazin-1-yl)ethyl)cyclopropanamine;
   (trans)-N-(2-(4-methylpiperazin-1-yl)ethyl)-2-(3'-(trifluoromethyl)biphenyl-4-yl)cyclopropanamine;
   (trans)-2-(3'-chlorobiphenyl-4-yl)-N-(2-(4-methylpiperazin-1-yl)ethyl)cyclopropanamine;

(R)-1-(2-((trans)-2-(3'-(trifluoromethyl)biphenyl-4-yl)cyclopropylamino)ethyl)pyrrolidin-3-amine;

N$^1$-cyclopropyl-N$^2$-((trans)-2-(3'-(trifluoromethyl)biphenyl-4-yl)cyclopropyl)ethane-1,2-diamine;

N-4-fluorobenzyl-N-{(trans)-2-[4-(benzyloxy)phenyl]cyclopropyl}amine;

N-4-methoxybenzyl-N-{(trans)-2-[4-(benzyloxy)phenyl]cyclopropyl}amine;

N-benzyl-N-{(trans)-2-[4-(benzyloxy)phenyl]cyclopropyl}amine,

N-[(trans)-2-phenylcyclopropyl]amino-methyl)pyridin-3-ol;

N-[(trans)-2-phenylcyclopropyl]-N-(3-methylpyridin-2-ylmethyl)amine;

N-[(trans)-2-phenylcyclopropyl]-N-(4-chloropyridin-3-ylmethyl)amine;

N-[(trans)-2-phenylcyclopropyl]-N-(4-trifluoromethyl-pyridin-3-ylmethyl)amine;

N-(3-methoxybenzyl)-N-[(trans)-2-phenylcyclopropyl]amine;

N-[(trans)-2-phenylcyclopropyl]-N-(quinolin-4-ylmethyl)amine;

N-(2-fluorobenzyl)-N-[(trans)-2-phenylcyclopropyl]amine;

N-(3-fluorobenzyl)-N-[(trans)-2-phenylcyclopropyl]amine;

N-[(trans)-2-phenylcyclopropyl]-N-(3,4-dichloro-1-phenylmethyl)amine;

N-[(trans)-2-phenylcyclopropyl]-N-(5-bromo-thiophen-2-ylmethyl)amine;

N-[(trans)-2-phenylcyclopropyl]-N-(3-bromo-thiophen-2-ylmethyl)amine;

N-[(trans)-2-phenylcyclopropyl]-N-(thiophen-2-ylmethyl)amine;

N-[(trans)-2-phenylcyclopropyl]-N-(1,3-thiazol-2-ylmethyl)amine;

N-[(trans)-2-phenylcyclopropyl]-N-(pyridin-4-ylmethyl)amine;

N-[(trans)-2-phenylcyclopropyl]-N-(pyridin-3-ylmethyl)amine;

N-[(trans)-2-phenylcyclopropyl]-N-(pyridin-2-ylmethyl)amine;

[(trans)-2-phenylcyclopropyl]-N-[4-(trifluoromethyl)benzyl]amine;

({[(trans)-2-phenylcyclopropyl]amino}methyl)benzonitrile;

N-(4-fluorobenzyl)-N-[(trans)-2-phenylcyclopropyl]amine;

N-[(trans)-2-phenylcyclopropyl]-N-(3-bromo-pyridin-2-ylmethyl)amine;

N-4-cyanobenzyl-N-{(trans)-2-[4-(benzyloxy)phenyl]cyclopropyl}amine;

N-4-[(benzyloxy)-benzyl]-N-[(trans)-2-(4-phenyl)cyclopropyl]amine;

2-((trans)-2-(4-(4-cyanobenzyloxy)phenyl)cyclopropylamino)acetamide;

2-((trans)-2-(4-(3-cyanobenzyloxy)phenyl)cyclopropylamino)acetamide;

2-((trans)-2-(4-(benzyloxy)phenyl)cyclopropylamino)acetamide;

2-((trans)-2-(4-(4-fluorobenzyloxy)phenyl)cyclopropylamino)acetamide;

2-((trans)-2-(4-(3-fluorobenzyloxy)phenyl)cyclopropylamino)acetamide;

2-((trans)-2-(4-(3-chlorobenzyloxy)phenyl)cyclopropylamino)acetamide;

2-((trans)-2-(4-(4-chlorobenzyloxy)phenyl)cyclopropylamino)acetamide;

2-((trans)-2-(4-(3-bromobenzyloxy)phenyl)cyclopropylamino)acetamide;

2-((trans)-2-(4-(3,5-difluorobenzyloxy)phenyl)cyclopropylamino)acetamide;

2-((trans)-2-(4-phenethoxyphenyl)cyclopropylamino)acetamide;

2-((trans)-2-(3'-(trifluoromethyl)biphenyl-4-yl)cyclopropylamino)acetamide;

2-((trans)-2-(3'-chlorobiphenyl-4-yl)cyclopropylamino)acetamide;

2-((trans)-2-phenylcyclopropylamino)-N-(piperidin-4-ylmethyl)acetamide;

N-(1-(dimethylamino)propan-2-yl)-2-((trans)-2-phenylcyclopropylamino)acetamide;

1-((S)-3-(dimethylamino)pyrrolidin-1-yl)-2-((trans)-2-phenylcyclopropylamino)ethanone;

1-((R)-3-(dimethylamino)pyrrolidin-1-yl)-2-((trans)-2-phenylcyclopropylamino)ethanone;

1-((S)-3-aminopyrrolidin-1-yl)-2-((trans)-2-phenylcyclopropylamino)ethanone;

2-((trans)-2-phenylcyclopropylamino)-N—((R)-pyrrolidin-3-yl)acetamide;

2-((trans)-2-phenylcyclopropylamino)-N—((R)-pyrrolidin-3-yl)acetamide;

2-((trans)-2-(4-(4-chlorobenzyloxy)phenyl)cyclopropylamino)-1-(4-methylpiperazin-1-yl)ethanone;

2-((trans)-2-(4-(3-bromobenzyloxy)phenyl)cyclopropylamino)-1-(4-methylpiperazin-1-yl)ethanone;

4-((4-((trans)-2-(2-(4-methylpiperazin-1-yl)-2-oxoethylamino)cyclopropyl)phenoxy)methyl)benzonitrile;

2-((trans)-2-(4-(biphenyl-4-ylmethoxy)phenyl)cyclopropylamino)-1-(4-methylpiperazin-1-yl)ethanone;

2-((trans)-2-(4-pyridin-3-ylphenyl) cyclopropylamino)-1-(4-methylpiperazin-1-yl)ethanone;

2-((trans)-2-(3'-methoxy-1,1'-biphenyl-4-yl)cyclopropylamino)-1-(4-methylpiperazin-1-yl)ethanone;

2-((trans)-2-(4'-methoxybiphenyl-4-yl)cyclopropylamino)-1-(4-methylpiperazin-1-yl)ethanone;

4'-((trans)-2-(2-(4-methylpiperazin-1-yl)-2-oxoethylamino)cyclopropyl)biphenyl-3-carbonitrile;

4'-((trans)-2-(2-(4-methylpiperazin-1-yl)-2-oxoethylamino)cyclopropyl)biphenyl-4-carbonitrile;

2-((trans)-2-(4'-fluorobiphenyl-4-yl)cyclopropylamino)-1-(4-methylpiperazin-1-yl)ethanone;

1-(4-methylpiperazin-1-yl)-2-((trans)-2-(3'-(trifluoromethyl)biphenyl-4-yl)cyclopropylamino)ethanone;

1-(4-methylpiperazin-1-yl)-2-((trans)-2-(4'-(methylsulfonyl)biphenyl-4-yl)cyclopropylamino)ethanone;

2-((trans)-2-(3',5'-dichlorobiphenyl-4-yl)cyclopropylamino)-1-(4-methylpiperazin-1-yl)ethanone;

2-((trans)-2-(2',4'-difluorobiphenyl-4-yl)cyclopropylamino)-1-(4-methylpiperazin-1-yl)ethanone;

2-((trans)-2-(4-(6-methoxypyridin-3-yl)phenyl)cyclopropylamino)-1-(4-methylpiperazin-1-yl)ethanone;

2-((trans)-2-(2'-fluorobiphenyl-4-yl)cyclopropylamino)-1-(4-methylpiperazin-1-yl)ethanone;

1-(4-methylpiperazin-1-yl)-2-((trans)-2-(4'-(trifluoromethyl)biphenyl-4-yl)cyclopropylamino)ethanone;

1-(4-methylpiperazin-1-yl)-2-((trans)-2-(2'-(trifluoromethyl)biphenyl-4-yl)cyclopropylamino)ethanone;

1-(4-methylpiperazin-1-yl)-2-((trans)-2-(4'-(trifluoromethoxy)biphenyl-4-yl)cyclopropylamino)ethanone;

2-((trans)-2-(3'-fluorobiphenyl-4-yl)cyclopropylamino)-1-(4-methylpiperazin-1-yl)ethanone;

2-((trans)-2-(4'-fluoro-2'-methoxybiphenyl-4-yl)cyclopropylamino)-1-(4-methylpiperazin-1-yl)ethanone;
1-(4-methylpiperazin-1-yl)-2-((trans)-2-(4-(pyridin-4-yl)phenyl)cyclopropylamino)ethanone;
2-((trans)-2-(3'-chlorobiphenyl-4-yl)cyclopropylamino)-1-(4-methylpiperazin-1-yl)ethanone;
2-((trans)-2-(4'-chlorobiphenyl-4-yl)cyclopropylamino)-1-(4-methylpiperazin-1-yl)ethanone;
2-((trans)-2-(5'-fluoro-2'-(trifluoromethyl)biphenyl-4-yl)cyclopropylamino)-1-(4-methylpiperazin-1-yl)ethanone;
2-((trans)-2-(4-(2-methoxypyridin-3-yl)phenyl)cyclopropylamino)-1-(4-methylpiperazin-1-yl)ethanone;
1-(4-methylpiperazin-1-yl)-2-((trans)-2-(4-phenethylphenyl)cyclopropylamino)ethanone;
2-((trans)-2-(4-cyclopropylphenyl)cyclopropylamino)-1-(4-methylpiperazin-1-yl)ethanone;
(trans)-N-((6-methylpyridin-2-yl)methyl)-2-phenylcyclopropanamine;
(trans)-N-((4-bromothiophen-2-yl)methyl)-2-phenylcyclopropanamine;
(trans)-2-phenyl-N-((6-(trifluoromethyl)pyridin-3-yl)methyl)cyclopropanamine;
(trans)-N-((6-chloropyridin-3-yl)methyl)-2-phenylcyclopropanamine;
(trans)-N-((4-methylpyridin-2-yl)methyl)-2-phenylcyclopropanamine;
(trans)-N-((6-methoxypyridin-2-yl)methyl)-2-phenylcyclopropanamine;
(trans)-N-((6-bromopyridin-2-yl)methyl)-2-phenylcyclopropanamine;
(trans)-2-phenyl-N-(quinolin-2-ylmethyl)cyclopropanamine;
(trans)-2-phenyl-N-((5-(trifluoromethyl)pyridin-2-yl)methyl)cyclopropanamine;
(trans)-N-((3-fluoropyridin-2-yl)methyl)-2-phenylcyclopropanamine;
(trans)-2-phenyl-N-(quinolin-3-ylmethyl)cyclopropanamine;
(trans)-N-((6-methoxypyridin-3-yl)methyl)-2-phenylcyclopropanamine;
(trans)-N-((5-methoxypyridin-3-yl)methyl)-2-phenylcyclopropanamine;
(trans)-N-((2-methoxypyridin-3-yl)methyl)-2-phenylcyclopropanamine;
(trans)-N-((3H-indol-3-yl)methyl)-2-phenylcyclopropanamine;
3-(((trans)-2-phenylcyclopropylamino)methyl)benzonitrile;
(trans)-N-(2-methoxybenzyl)-2-phenylcyclopropanamine;
3-(((trans)-2-phenylcyclopropylamino)methyl)pyridin-2-amine;
(trans)-N-((2-chloropyridin-3-yl)methyl)-2-phenylcyclopropanamine;
(trans)-N-(3,4-dimethoxybenzyl)-2-phenylcyclopropanamine;
(trans)-N-((2,3-dihydrobenzofuran-5-yl)methyl)-2-phenylcyclopropanamine;
(trans)-N-(benzo[d][1,3]dioxol-5-ylmethyl)-2-phenylcyclopropanamine;
(trans)-N-((2,3-dihydrobenzo[b][1,4]dioxin-6-yl)methyl)-2-phenylcyclopropanamine;
(trans)-N-(2,6-difluoro-4-methoxybenzyl)-2-phenylcyclopropanamine;
(trans)-2-phenyl-N-(4-(trifluoromethoxy)benzyl)cyclopropanamine;
(trans)-N-(5-fluoro-2-methoxybenzyl)-2-phenylcyclopropanamine;
(trans)-N-(2-fluoro-4-methoxybenzyl)-2-phenylcyclopropanamine;
(trans)-N-((4-methoxynaphthalen-1-yl)methyl)-2-phenylcyclopropanamine;
(trans)-N-(2-fluoro-6-methoxybenzyl)-2-phenylcyclopropanamine;
(trans)-N-((2-methoxynaphthalen-1-yl)methyl)-2-phenylcyclopropanamine;
(trans)-N-((4,7-dimethoxynaphthalen-1-yl)methyl)-2-phenylcyclopropanamine;
(trans)-N-(4-methoxy-3-methylbenzyl)-2-phenylcyclopropanamine;
(trans)-N-(3-chloro-4-methoxybenzyl)-2-phenylcyclopropanamine;
(trans)-N-(3-fluoro-4-methoxybenzyl)-2-phenylcyclopropanamine;
(trans)-N-(4-methoxy-2-methylbenzyl)-2-phenylcyclopropanamine;
(trans)-N-((3,4-dihydro-2H-benzo[b][1,4]dioxepin-6-yl)methyl)-2-phenylcyclopropanamine;
(trans)-N-((3,4-dihydro-2H-benzo[b][1,4]dioxepin-7-yl)methyl)-2-phenylcyclopropanamine;
(trans)-N-((2,2-dimethylchroman-6-yl)methyl)-2-phenylcyclopropanamine;
(trans)-N-(4-methoxy-2,3-dimethylbenzyl)-2-phenylcyclopropanamine;
(trans)-N-(4-methoxy-2,5-dimethylbenzyl)-2-phenylcyclopropanamine;
(trans)-N-(2-fluoro-4,5-dimethoxybenzyl)-2-phenylcyclopropanamine;
(trans)-N-(3-chloro-4,5-dimethoxybenzyl)-2-phenylcyclopropanamine;
(trans)-N-(2-chloro-3,4-dimethoxybenzyl)-2-phenylcyclopropanamine;
(trans)-N-(2,4-di methoxy-6-methylbenzyl)-2-phenylcyclopropanamine;
(trans)-N-(2,5-dimethoxybenzyl)-2-phenylcyclopropanamine;
(trans)-N-(2,3-dimethoxybenzyl)-2-phenylcyclopropanamine;
(trans)-N-(2-chloro-3-methoxybenzyl)-2-phenylcyclopropanamine;
(trans)-N-((1H-indol-5-yl)methyl)-2-phenylcyclopropanamine;
(trans)-2-(4-(benzyloxy)phenyl)-N-(pyridin-2-ylmethyl)cyclopropanamine;
(trans)-2-(4-(benzyloxy)phenyl)-N-(2-methoxybenzyl)cyclopropanamine;
(trans)-N-(1-(3,4-dimethoxyphenyl)ethyl)-2-phenylcyclopropanamine;
(trans)-N-(1-(2,3-dihydrobenzo[b][1,4]dioxin-6-yl)ethyl)-2-phenylcyclopropanamine;
(trans)-N-(1-(5-fluoro-2-methoxyphenyl)ethyl)-2-phenylcyclopropanamine;
(trans)-N-(1-(3,4-dimethoxyphenyl)propan-2-yl)-2-phenylcyclopropanamine;
(trans)-N-((3-methyl-1,2,4-oxadiazol-5-yl)methyl)-2-phenylcyclopropanamine;
N-(trans)-2-(isobutylthio)-ethyl-2-phenylcyclopropanamine;
N-trans-(2-ethoxyethyl)-2-phenylcyclopropanamine;
N-trans-(2-methoxyethyl)-2-phenylcyclopropanamine;
N1-((trans)-2-(4-(3-bromobenzyloxy)phenyl)cyclopropyl)-N2-cyclopropylethane-1,2-diamine;

N1-((trans)-2-(3'-chlorobiphenyl-4-yl)cyclopropyl)-N2-cyclopropylethane-1,2-diamine;
N1-cyclopropyl-N2-((trans)-2-(4-phenethoxyphenyl)cyclopropyl)ethane-1,2-diamine;
N1,N1-diethyl-N2-((trans)-2-(4-(3-fluorobenzyloxy)phenyl)cyclopropyl)ethane-1,2-diamine;
(trans)-2-(4-bromophenyl)-N-(2-(4-methylpiperazin-1-yl)ethyl)cyclopropanamine;
(trans)-N-(2-(piperidin-1-yl)ethyl)-2-(3'-(trifluoromethyl)biphenyl-4-yl)cyclopropanamine;
N1,N1-diethyl-N2-((trans)-2-(3'-(trifluoromethyl)biphenyl-4-yl)cyclopropyl)ethane-1,2-diamine;
(trans)-N-(2-(piperazin-1-yl)ethyl)-2-(3'-(trifluoromethyl)biphenyl-4-yl)cyclopropanamine;
(S)-1-(2-((trans)-2-(3'-(trifluoromethyl)biphenyl-4-yl)cyclopropylamino)ethyl)pyrrolidin-3-amine;
(R)-1-(2-((trans)-2-(3'-chlorobiphenyl-4-yl)cyclopropylamino)ethyl)pyrrolidin-3-amine;
(R)-1-(2-((trans)-2-(4'-chlorobiphenyl-4-yl)cyclopropylamino)ethyl)pyrrolidin-3-amine;
(R)-1-(2-((trans)-2-(3'-methoxybiphenyl-4-yl)cyclopropylamino)ethyl)pyrrolidin-3-amine;
(R)-1-(2-((trans)-2-(4-(3-bromobenzyloxy)phenyl)cyclopropylamino)ethyl)pyrrolidin-3-amine; and
(R)-1-(2-((trans)-2-(6-(3-(trifluoromethyl)phenyl)pyridin-3-yl)cyclopropylamino)ethyl)pyrrolidin-3-amine;
or a pharmaceutically acceptable salt thereof.

2. A method of treating a viral infection selected from a herpesvirus or adenovirus in a mammal that has undergone, is undergoing, or will undergo an organ or tissue transplant, the method comprising administering a therapeutically effective amount of a potent selective LSD1 inhibitor (lysine-specific demethylase-1) or a LSD1/MAO-B (monoamine oxidase-B) dual inhibitor, or a pharmaceutically acceptable salt thereof, wherein the potent selective LSD1 inhibitor or LSD1/MAO-B dual inhibitor is a cyclopropylamine acetamide derivative or a cyclopropylamine derivative selected from the group consisting of:
N-cyclopropyl-2-{[(trans)-2-phenylcyclopropyl]amino}acetamide;
2-{[(trans)-2-phenylcyclopropyl]amino}acetamide;
N-cyclopropyl-2-{[(trans)-2-phenylcyclopropyl]amino}propanamide;
2-{[(trans)-2-phenylcyclopropyl]amino}-N-prop-2-ynyl-acetamide;
N-(2-morpholin-4-yl-2-oxoethyl)-N-[(trans)-2-phenylcyclopropyl]amine;
2-{[(trans)-2-phenylcyclopropyl]amino}propanamide;
Methyl 2-{[(trans)-2-phenylcyclopropyl]amino}propanoate;
1-(4-methylpiperazin-1-yl)-2-((trans)-2-phenylcyclopropylamino)ethanone;
1-(4-ethylpiperazin-1-yl)-2-((trans)-2-phenylcyclopropylamino)ethanone;
1-(4-benzylpiperazin-1-yl)-2-((trans)-2-phenylcyclopropylamino)ethanone;
2-((trans)-2-phenylcyclopropylamino)-1-(4-phenylpiperazin-1-yl)ethanone;
2-((trans)-2-(4-(benzyloxy)phenyl)cyclopropylamino)-1-(4-methylpiperazin-1-yl)ethanone;
2-((trans)-2-(1,1'-biphenyl-4-yl)cyclopropylamino)-1-(4-methylpiperazin-1-yl)ethanone;
2-((trans)-2-(4-(benzyloxy)phenyl)cyclopropylamino)-N-cyclopropylacetamide;
2-((trans)-2-(4-(3-fluorobenzyloxy)phenyl)cyclopropylamino)-1-(4-methylpiperazin-1-yl)ethanone;
2-((trans)-2-(4-(4-fluorobenzyloxy)phenyl)cyclopropylamino)-1-(4-methylpiperazin-1-yl)ethanone;
2-((trans)-2-(4-(3-chlorobenzyloxy)phenyl)cyclopropylamino)-1-(4-methylpiperazin-1-yl)ethanone;
1-(4-methylpiperazin-1-yl)-2-((trans)-2-(4-phenethoxyphenyl) cyclopropylamino)ethanone;
2-((trans)-2-(biphenyl-4-yl)cyclopropylamino)-1-(4-methylpiperazin-1-yl)ethanone;
N-[2-(4-methylpiperazin-1-yl)ethyl]-N-[(trans)-2-phenylcyclopropyl]amine;
N-cyclopropyl-N'-[(trans)-2-phenylcyclopropyl]ethane-1,2-diamine;
N,N-dimethyl-N'-(2-{[(trans)-2-phenylcyclopropyl]amino}ethyl)ethane-1,2-diamine;
(3R)-1-(2-{[(trans)-2-phenylcyclopropyl]amino}ethyl)pyrrolidin-3-amine;
(3S)—N,N-dimethyl-1-(2-{[(trans)-2-phenylcyclopropyl]amino}ethyl)pyrrolidin-3-amine;
(3R)—N,N-dimethyl-1-(2-{[(trans)-2-phenylcyclopropyl]amino}ethyl)pyrrolidin-3-amine;
N-[(trans)-2-phenylcyclopropyl]-N-(2-piperazin-1-ylethyl)amine;
N,N-diethyl-N'-[(trans)-2-phenylcyclopropyl]ethane-1,2-diamine;
N-[(trans)-2-phenylcyclopropyl]-N-(2-piperidin-1-ylethyl)amine;
(trans)-2-(4-(benzyloxy)phenyl)-N-(2-(4-methylpiperazin-1-yl)ethyl)cyclopropanamine;
(trans)-N-(2-(4-methylpiperazin-1-yl)ethyl)-2-(3'-(trifluoromethyl)biphenyl-4-yl)cyclopropanamine;
(trans)-2-(3'-chlorobiphenyl-4-yl)-N-(2-(4-methylpiperazin-1-yl)ethyl)cyclopropanamine;
(R)-1-(2-((trans)-2-(3'-(trifluoromethyl)biphenyl-4-yl)cyclopropylamino)ethyl)pyrrolidin-3-amine;
$N^1$-cyclopropyl-$N^2$-((trans)-2-(3'-(trifluoromethyl)biphenyl-4-yl)cyclopropyl)ethane-1,2-diamine;
N-4-fluorobenzyl-N-{(trans)-2-[4-(benzyloxy)phenyl]cyclopropyl}amine;
N-4-methoxybenzyl-N-{(trans)-2-[4-(benzyloxy)phenyl]cyclopropyl}amine;
N-benzyl-N-{(trans)-2-[4-(benzyloxy)phenyl]cyclopropyl}amine,
N-[(trans)-2-phenylcyclopropyl]amino-methyl)pyridin-3-ol;
N-[(trans)-2-phenylcyclopropyl]-N-(3-methylpyridin-2-ylmethyl)amine;
N-[(trans)-2-phenylcyclopropyl]-N-(4-chloropyridin-3-ylmethyl)amine;
N-[(trans)-2-phenylcyclopropyl]-N-(4-trifluoromethyl-pyridin-3-ylmethyl)amine;
N-(3-methoxybenzyl)-N-[(trans)-2-phenylcyclopropyl]amine;
N-[(trans)-2-phenylcyclopropyl]-N-(quinolin-4-ylmethyl)amine;
N-(2-fluorobenzyl)-N-[(trans)-2-phenylcyclopropyl]amine;
N-(3-fluorobenzyl)-N-[(trans)-2-phenylcyclopropyl]amine;
N-[(trans)-2-phenylcyclopropyl]-N-(3,4-dichloro-1-phenylmethyl)amine;
N-[(trans)-2-phenylcyclopropyl]-N-(5-bromo-thiophen-2-ylmethyl)amine;
N-[(trans)-2-phenylcyclopropyl]-N-(3-bromo-thiophen-2-ylmethyl)amine;
N-[(trans)-2-phenylcyclopropyl]-N-(thiophen-2-ylmethyl)amine;

N-[(trans)-2-phenylcyclopropyl]-N-(1,3-thiazol-2-ylmethyl)amine;
N-[(trans)-2-phenylcyclopropyl]-N-(pyridin-4-ylmethyl)amine;
N-[(trans)-2-phenylcyclopropyl]-N-(pyridin-3-ylmethyl)amine;
N-[(trans)-2-phenylcyclopropyl]-N-(pyridin-2-ylmethyl)amine;
[(trans)-2-phenylcyclopropyl]-N-[4-(trifluoromethyl)benzyl]amine;
({[(trans)-2-phenylcyclopropyl]amino}methyl)benzonitrile;
N-(4-fluorobenzyl)-N-[(trans)-2-phenylcyclopropyl]amine;
N-[(trans)-2-phenylcyclopropyl]-N-(3-bromo-pyridin-2-ylmethyl)amine;
N-4-cyanobenzyl-N-{(trans)-2-[4-(benzyloxy)phenyl]cyclopropyl}amine;
N-4-[(benzyloxy)-benzyl]-N-[(trans)-2-(4-phenyl)cyclopropyl]amine;
2-((trans)-2-(4-(4-cyanobenzyloxy)phenyl)cyclopropylamino)acetamide;
2-((trans)-2-(4-(3-cyanobenzyloxy)phenyl)cyclopropylamino)acetamide;
2-((trans)-2-(4-(benzyloxy)phenyl)cyclopropylamino)acetamide;
2-((trans)-2-(4-(4-fluorobenzyloxy)phenyl)cyclopropylamino)acetamide;
2-((trans)-2-(4-(3-fluorobenzyloxy)phenyl)cyclopropylamino)acetamide;
2-((trans)-2-(4-(3-chlorobenzyloxy)phenyl)cyclopropylamino)acetamide;
2-((trans)-2-(4-(4-chlorobenzyloxy)phenyl)cyclopropylamino)acetamide;
2-((trans)-2-(4-(3-bromobenzyloxy)phenyl)cyclopropylamino)acetamide;
2-((trans)-2-(4-(3,5-difluorobenzyloxy)phenyl)cyclopropylamino)acetamide;
2-((trans)-2-(4-phenethoxyphenyl)cyclopropylamino)acetamide;
2-((trans)-2-(3'-(trifluoromethyl)biphenyl-4-yl)cyclopropylamino)acetamide;
2-((trans)-2-(3'-chlorobiphenyl-4-yl)cyclopropylamino)acetamide;
2-((trans)-2-phenylcyclopropylamino)-N-(piperidin-4-ylmethyl)acetamide;
N-(1-(dimethylamino)propan-2-yl)-2-((trans)-2-phenylcyclopropylamino)acetamide;
1-((S)-3-(dimethylamino)pyrrolidin-1-yl)-2-((trans)-2-phenylcyclopropylamino)ethanone;
1-((R)-3-(dimethylamino)pyrrolidin-1-yl)-2-((trans)-2-phenylcyclopropylamino)ethanone;
1-((S)-3-aminopyrrolidin-1-yl)-2-((trans)-2-phenylcyclopropylamino)ethanone;
2-((trans)-2-phenylcyclopropylamino)-N—((R)-pyrrolidin-3-yl)acetamide;
2-((trans)-2-phenylcyclopropylamino)-N—((R)-pyrrolidin-3-yl)acetamide;
2-((trans)-2-(4-(4-chlorobenzyloxy)phenyl)cyclopropylamino)-1-(4-methylpiperazin-1-yl)ethanone;
2-((trans)-2-(4-(3-bromobenzyloxy)phenyl)cyclopropylamino)-1-(4-methylpiperazin-1-yl)ethanone;
4-((4-((trans)-2-(2-(4-methylpiperazin-1-yl)-2-oxoethylamino)cyclopropyl)phenoxy)methyl)benzonitrile;
2-((trans)-2-(4-(biphenyl-4-ylmethoxy)phenyl)cyclopropylamino)-1-(4-methylpiperazin-1-yl)ethanone;
2-((trans)-2-(4-pyridin-3-ylphenyl) cyclopropylamino)-1-(4-methylpiperazin-1-yl)ethanone;
2-((trans)-2-(3'-methoxy-1,1'-biphenyl-4-yl)cyclopropylamino)-1-(4-methylpiperazin-1-yl)ethanone;
2-((trans)-2-(4'-methoxybiphenyl-4-yl)cyclopropylamino)-1-(4-methylpiperazin-1-yl)ethanone;
4'-((trans)-2-(2-(4-methylpiperazin-1-yl)-2-oxoethylamino)cyclopropyl)biphenyl-3-carbonitrile;
4'-((trans)-2-(2-(4-methylpiperazin-1-yl)-2-oxoethylamino)cyclopropyl)biphenyl-4-carbonitrile;
2-((trans)-2-(4'-fluorobiphenyl-4-yl)cyclopropylamino)-1-(4-methylpiperazin-1-yl)ethanone;
1-(4-methylpiperazin-1-yl)-2-((trans)-2-(3'-(trifluoromethyl)biphenyl-4-yl)cyclopropylamino)ethanone;
1-(4-methylpiperazin-1-yl)-2-((trans)-2-(4'-(methylsulfonyl)biphenyl-4-yl)cyclopropylamino)ethanone;
2-((trans)-2-(3',5'-dichlorobiphenyl-4-yl)cyclopropylamino)-1-(4-methylpiperazin-1-yl)ethanone;
2-((trans)-2-(2',4'-difluorobiphenyl-4-yl)cyclopropylamino)-1-(4-methylpiperazin-1-yl)ethanone;
2-((trans)-2-(4-(6-methoxypyridin-3-yl)phenyl)cyclopropylamino)-1-(4-methylpiperazin-1-yl)ethanone;
2-((trans)-2-(2'-fluorobiphenyl-4-yl)cyclopropylamino)-1-(4-methylpiperazin-1-yl)ethanone;
1-(4-methylpiperazin-1-yl)-2-((trans)-2-(4'-(trifluoromethyl)biphenyl-4-yl)cyclopropylamino)ethanone;
1-(4-methylpiperazin-1-yl)-2-((trans)-2-(2'-(trifluoromethyl)biphenyl-4-yl)cyclopropylamino)ethanone;
1-(4-methylpiperazin-1-yl)-2-((trans)-2-(4'-(trifluoromethoxy)biphenyl-4-yl)cyclopropylamino)ethanone;
2-((trans)-2-(3'-fluorobiphenyl-4-yl)cyclopropylamino)-1-(4-methylpiperazin-1-yl)ethanone;
2-((trans)-2-(4'-fluoro-2'-methoxybiphenyl-4-yl)cyclopropylamino)-1-(4-methylpiperazin-1-yl)ethanone;
1-(4-methylpiperazin-1-yl)-2-((trans)-2-(4-(pyridin-4-yl)phenyl)cyclopropylamino)ethanone;
2-((trans)-2-(3'-chlorobiphenyl-4-yl)cyclopropylamino)-1-(4-methylpiperazin-1-yl)ethanone;
2-((trans)-2-(4'-chlorobiphenyl-4-yl)cyclopropylamino)-1-(4-methylpiperazin-1-yl)ethanone;
2-((trans)-2-(5'-fluoro-2'-(trifluoromethyl)biphenyl-4-yl)cyclopropylamino)-1-(4-methylpiperazin-1-yl)ethanone;
2-((trans)-2-(4-(2-methoxypyridin-3-yl)phenyl)cyclopropylamino)-1-(4-methylpiperazin-1-yl)ethanone;
1-(4-methylpiperazin-1-yl)-2-((trans)-2-(4-phenethylphenyl)cyclopropylamino)ethanone;
2-((trans)-2-(4-cyclopropylphenyl)cyclopropylamino)-1-(4-methylpiperazin-1-yl)ethanone;
(trans)-N-((6-methylpyridin-2-yl)methyl)-2-phenylcyclopropanamine;
(trans)-N-((4-bromothiophen-2-yl)methyl)-2-phenylcyclopropanamine;
(trans)-2-phenyl-N-((6-(trifluoromethyl)pyridin-3-yl)methyl)cyclopropanamine;
(trans)-N-((6-chloropyridin-3-yl)methyl)-2-phenylcyclopropanamine;
(trans)-N-((4-methylpyridin-2-yl)methyl)-2-phenylcyclopropanamine;
(trans)-N-((6-methoxypyridin-2-yl)methyl)-2-phenylcyclopropanamine;
(trans)-N-((6-bromopyridin-2-yl)methyl)-2-phenylcyclopropanamine;
(trans)-2-phenyl-N-(quinolin-2-ylmethyl)cyclopropanamine;
(trans)-2-phenyl-N-((5-(trifluoromethyl)pyridin-2-yl)methyl)cyclopropanamine;

(trans)-N-((3-fluoropyridin-2-yl)methyl)-2-phenylcyclopropanamine;
(trans)-2-phenyl-N-(quinolin-3-ylmethyl)cyclopropanamine;
(trans)-N-((6-methoxypyridin-3-yl)methyl)-2-phenylcyclopropanamine;
(trans)-N-((5-methoxypyridin-3-yl)methyl)-2-phenylcyclopropanamine;
(trans)-N-((2-methoxypyridin-3-yl)methyl)-2-phenylcyclopropanamine;
(trans)-N-((3H-indol-3-yl)methyl)-2-phenylcyclopropanamine;
3-(((trans)-2-phenylcyclopropylamino)methyl)benzonitrile;
(trans)-N-(2-methoxybenzyl)-2-phenylcyclopropanamine;
3-(((trans)-2-phenylcyclopropylamino)methyl)pyridin-2-amine;
(trans)-N-((2-chloropyridin-3-yl)methyl)-2-phenylcyclopropanamine;
(trans)-N-(3,4-dimethoxybenzyl)-2-phenylcyclopropanamine;
(trans)-N-((2,3-dihydrobenzofuran-5-yl)methyl)-2-phenylcyclopropanamine;
(trans)-N-(benzo[d][1,3]dioxol-5-ylmethyl)-2-phenylcyclopropanamine;
(trans)-N-((2,3-dihydrobenzo[b][1,4]dioxin-6-yl)methyl)-2-phenylcyclopropanamine;
(trans)-N-(2,6-difluoro-4-methoxybenzyl)-2-phenylcyclopropanamine;
(trans)-2-phenyl-N-(4-(trifluoromethoxy)benzyl)cyclopropanamine;
(trans)-N-(5-fluoro-2-methoxybenzyl)-2-phenylcyclopropanamine;
(trans)-N-(2-fluoro-4-methoxybenzyl)-2-phenylcyclopropanamine;
(trans)-N-((4-methoxynaphthalen-1-yl)methyl)-2-phenylcyclopropanamine;
(trans)-N-(2-fluoro-6-methoxybenzyl)-2-phenylcyclopropanamine;
(trans)-N-((2-methoxynaphthalen-1-yl)methyl)-2-phenylcyclopropanamine;
(trans)-N-((4,7-dimethoxynaphthalen-1-yl)methyl)-2-phenylcyclopropanamine;
(trans)-N-(4-methoxy-3-methylbenzyl)-2-phenylcyclopropanamine;
(trans)-N-(3-chloro-4-methoxybenzyl)-2-phenylcyclopropanamine;
(trans)-N-(3-fluoro-4-methoxybenzyl)-2-phenylcyclopropanamine;
(trans)-N-(4-methoxy-2-methylbenzyl)-2-phenylcyclopropanamine;
(trans)-N-((3,4-dihydro-2H-benzo[b][1,4]dioxepin-6-yl)methyl)-2-phenylcyclopropanamine;
(trans)-N-((3,4-dihydro-2H-benzo[b][1,4]dioxepin-7-yl)methyl)-2-phenylcyclopropanamine;
(trans)-N-((2,2-dimethylchroman-6-yl)methyl)-2-phenylcyclopropanamine;
(trans)-N-(4-methoxy-2,3-dimethylbenzyl)-2-phenylcyclopropanamine;
(trans)-N-(4-methoxy-2,5-dimethylbenzyl)-2-phenylcyclopropanamine;
(trans)-N-(2-fluoro-4,5-dimethoxybenzyl)-2-phenylcyclopropanamine;
(trans)-N-(3-chloro-4,5-dimethoxybenzyl)-2-phenylcyclopropanamine;
(trans)-N-(2-chloro-3,4-dimethoxybenzyl)-2-phenylcyclopropanamine;
(trans)-N-(2,4-di methoxy-6-methyl benzyl)-2-phenylcyclopropanamine;
(trans)-N-(2,5-dimethoxybenzyl)-2-phenylcyclopropanamine;
(trans)-N-(2,3-dimethoxybenzyl)-2-phenylcyclopropanamine;
(trans)-N-(2-chloro-3-methoxybenzyl)-2-phenylcyclopropanamine;
(trans)-N-((1H-indol-5-yl)methyl)-2-phenylcyclopropanamine;
(trans)-2-(4-(benzyloxy)phenyl)-N-(pyridin-2-ylmethyl)cyclopropanamine;
(trans)-2-(4-(benzyloxy)phenyl)-N-(2-methoxybenzyl)cyclopropanamine;
(trans)-N-(1-(3,4-dimethoxyphenyl)ethyl)-2-phenylcyclopropanamine;
(trans)-N-(1-(2,3-dihydrobenzo[b][1,4]dioxin-6-yl)ethyl)-2-phenylcyclopropanamine;
(trans)-N-(1-(5-fluoro-2-methoxyphenyl)ethyl)-2-phenylcyclopropanamine;
(trans)-N-(1-(3,4-dimethoxyphenyl)propan-2-yl)-2-phenylcyclopropanamine;
(trans)-N-((3-methyl-1,2,4-oxadiazol-5-yl)methyl)-2-phenylcyclopropanamine;
N-(trans)-2-(isobutylthio)-ethyl-2-phenylcyclopropanamine;
N-trans-(2-ethoxyethyl)-2-phenylcyclopropanamine;
N-trans-(2-methoxyethyl)-2-phenylcyclopropanamine;
N1-((trans)-2-(4-(3-bromobenzyloxy)phenyl)cyclopropyl)-N2-cyclopropylethane-1,2-diamine;
N1-((trans)-2-(3'-chlorobiphenyl-4-yl)cyclopropyl)-N2-cyclopropylethane-1,2-diamine;
N1-cyclopropyl-N2-((trans)-2-(4-phenethoxyphenyl)cyclopropyl)ethane-1,2-diamine;
N1,N1-diethyl-N2-((trans)-2-(4-(3-fluorobenzyloxy)phenyl)cyclopropyl)ethane-1,2-diamine;
(trans)-2-(4-bromophenyl)-N-(2-(4-methylpiperazin-1-yl)ethyl)cyclopropanamine;
(trans)-N-(2-(piperidin-1-yl)ethyl)-2-(3'-(trifluoromethyl)biphenyl-4-yl)cyclopropanamine;
N1,N1-diethyl-N2-((trans)-2-(3'-(trifluoromethyl)biphenyl-4-yl)cyclopropyl)ethane-1,2-diamine;
(trans)-N-(2-(piperazin-1-yl)ethyl)-2-(3'-(trifluoromethyl)biphenyl-4-yl)cyclopropanamine;
(S)-1-(2-((trans)-2-(3'-(trifluoromethyl)biphenyl-4-yl)cyclopropylamino)ethyl)pyrrolidin-3-amine;
(R)-1-(2-((trans)-2-(3'-chlorobiphenyl-4-yl)cyclopropylamino)ethyl)pyrrolidin-3-amine;
(R)-1-(2-((trans)-2-(4'-chlorobiphenyl-4-yl)cyclopropylamino)ethyl)pyrrolidin-3-amine;
(R)-1-(2-((trans)-2-(3'-methoxybiphenyl-4-yl)cyclopropylamino)ethyl)pyrrolidin-3-amine;
(R)-1-(2-((trans)-2-(4-(3-bromobenzyloxy)phenyl)cyclopropylamino)ethyl)pyrrolidin-3-amine; and
(R)-1-(2-((trans)-2-(6-(3-(trifluoromethyl)phenyl)pyridin-3-yl)cyclopropylamino)ethyl)pyrrolidin-3-amine;
or a pharmaceutically acceptable salt thereof.

3. The method according to any one of claims 1 and 2, wherein the mammal is a human.

4. The method according to any one of claims 1 and 2 wherein the viral infection is an herpes simplex virus type 1 (HSV1) infection.

5. The method according to any one of claims 1 and 2, wherein the viral infection is an herpes simplex virus type 2 (HSV2) infection.

6. The method according to any one of claims 1 and 2, wherein the viral infection is an Epstein-Barr virus (EBV) infection.

7. The method according to any one of claims 1 and 2, wherein the viral infection is a varicella zoster virus (VZV) infection.

8. The method according to claim 1, wherein the cyclopropylamine acetamide derivative or the cyclopropylamine derivative is selected from the group consisting of:

N-cyclopropyl-2-{[(trans)-2-phenylcyclopropyl]amino}acetamide;
2-{[(trans)-2-phenylcyclopropyl]amino}acetamide;
N-cyclopropyl-2-{[(trans)-2-phenylcyclopropyl]amino}propanamide;
2-{[(trans)-2-phenylcyclopropyl]amino}-N-prop-2-ynylacetamide;
N-(2-morpholin-4-yl-2-oxoethyl)-N-[(trans)-2-phenylcyclopropyl]amine;
2-{[(trans)-2-phenylcyclopropyl]amino}propanamide;
Methyl 2-{[(trans)-2-phenylcyclopropyl]amino}propanoate;
1-(4-methylpiperazin-1-yl)-2-((trans)-2-phenylcyclopropylamino)ethanone;
1-(4-ethylpiperazin-1-yl)-2-((trans)-2-phenylcyclopropylamino)ethanone;
1-(4-benzylpiperazin-1-yl)-2-((trans)-2-phenylcyclopropylamino)ethanone;
2-((trans)-2-phenylcyclopropylamino)-1-(4-phenylpiperazin-1-yl)ethanone;
2-((trans)-2-(4-(benzyloxy)phenyl)cyclopropylamino)-1-(4-methylpiperazin-1-yl)ethanone;
2-((trans)-2-(1,1'-biphenyl-4-yl)cyclopropylamino)-1-(4-methylpiperazin-1-yl)ethanone;
2-((trans)-2-(4-(benzyloxy)phenyl)cyclopropylamino)-N-cyclopropylacetamide;
2-((trans)-2-(4-(3-fluorobenzyloxy)phenyl)cyclopropylamino)-1-(4-methylpiperazin-1-yl)ethanone;
2-((trans)-2-(4-(4-fluorobenzyloxy)phenyl)cyclopropylamino)-1-(4-methylpiperazin-1-yl)ethanone;
2-((trans)-2-(4-(3-chlorobenzyloxy)phenyl)cyclopropylamino)-1-(4-methylpiperazin-1-yl)ethanone;
1-(4-methylpiperazin-1-yl)-2-((trans)-2-(4-phenethoxyphenyl) cyclopropylamino)ethanone;
2-((trans)-2-(biphenyl-4-yl)cyclopropylamino)-1-(4-methylpiperazin-1-yl)ethanone;
N-[2-(4-methylpiperazin-1-yl)ethyl]-N-[(trans)-2-phenylcyclopropyl]amine;
N-cyclopropyl-N'-[(trans)-2-phenylcyclopropyl]ethane-1,2-diamine;
N,N-dimethyl-N'-(2-{[(trans)-2-phenylcyclopropyl]amino}ethyl)ethane-1,2-diamine;
(3R)-1-(2-{[(trans)-2-phenylcyclopropyl]amino}ethyl)pyrrolidin-3-amine;
(3S)—N,N-dimethyl-1-(2-{[(trans)-2-phenylcyclopropyl]amino}ethyl)pyrrolidin-3-amine;
(3R)—N,N-dimethyl-1-(2-{[(trans)-2-phenylcyclopropyl]amino}ethyl)pyrrolidin-3-amine;
N-[(trans)-2-phenylcyclopropyl]-N-(2-piperazin-1-ylethyl)amine;
N,N-diethyl-N'-[(trans)-2-phenylcyclopropyl]ethane-1,2-diamine;
N-[(trans)-2-phenylcyclopropyl]-N-(2-piperidin-1-ylethyl)amine;
(trans)-2-(4-(benzyloxy)phenyl)-N-(2-(4-methylpiperazin-1-yl)ethyl)cyclopropanamine;
(trans)-N-(2-(4-methylpiperazin-1-yl)ethyl)-2-(3'-(trifluoromethyl)biphenyl-4-yl)cyclopropanamine;
(trans)-2-(3'-chlorobiphenyl-4-yl)-N-(2-(4-methylpiperazin-1-yl)ethyl)cyclopropanamine;
(R)-1-(2-((trans)-2-(3'-(trifluoromethyl)biphenyl-4-yl)cyclopropylamino)ethyl)pyrrolidin-3-amine;
$N^1$-cyclopropyl-$N^2$-((trans)-2-(3'-(trifluoromethyl)biphenyl-4-yl)cyclopropyl)ethane-1,2-diamine;
N-4-fluorobenzyl-N-{(trans)-2-[4-(benzyloxy)phenyl]cyclopropyl}amine;
N-4-methoxybenzyl-N-{(trans)-2-[4-(benzyloxy)phenyl]cyclopropyl}amine;
N-benzyl-N-{(trans)-2-[4-(benzyloxy)phenyl]cyclopropyl}amine,
N-[(trans)-2-phenylcyclopropyl]amino-methyl)pyridin-3-ol;
N-[(trans)-2-phenylcyclopropyl]-N-(3-methylpyridin-2-ylmethyl)amine;
N-[(trans)-2-phenylcyclopropyl]-N-(4-chloropyridin-3-ylmethyl)amine;
N-[(trans)-2-phenylcyclopropyl]-N-(4-trifluoromethyl-pyridin-3-ylmethyl)amine;
N-(3-methoxybenzyl)-N-[(trans)-2-phenylcyclopropyl]amine;
N-[(trans)-2-phenylcyclopropyl]-N-(quinolin-4-ylmethyl)amine;
N-(2-fluorobenzyl)-N-[(trans)-2-phenylcyclopropyl]amine;
N-(3-fluorobenzyl)-N-[(trans)-2-phenylcyclopropyl]amine;
N-[(trans)-2-phenylcyclopropyl]-N-(3,4-dichloro-1-phenylmethyl)amine;
N-[(trans)-2-phenylcyclopropyl]-N-(5-bromo-thiophen-2-ylmethyl)amine;
N-[(trans)-2-phenylcyclopropyl]-N-(3-bromo-thiophen-2-ylmethyl)amine;
N-[(trans)-2-phenylcyclopropyl]-N-(thiophen-2-ylmethyl)amine;
N-[(trans)-2-phenylcyclopropyl]-N-(1,3-thiazol-2-ylmethyl)amine;
N-[(trans)-2-phenylcyclopropyl]-N-(pyridin-4-ylmethyl)amine;
N-[(trans)-2-phenylcyclopropyl]-N-(pyridin-3-ylmethyl)amine;
N-[(trans)-2-phenylcyclopropyl]-N-(pyridin-2-ylmethyl)amine;
[(trans)-2-phenylcyclopropyl]-N-[4-(trifluoromethyl)benzyl]amine;
({[(trans)-2-phenylcyclopropyl]amino}methyl)benzonitrile;
N-(4-fluorobenzyl)-N-[(trans)-2-phenylcyclopropyl]amine;
N-[(trans)-2-phenylcyclopropyl]-N-(3-bromo-pyridin-2-ylmethyl)amine;
N-4-cyanobenzyl-N-{(trans)-2-[4-(benzyloxy)phenyl]cyclopropyl}amine;
N-4-[(benzyloxy)-benzyl]-N-[(trans)-2-(4-phenyl)cyclopropyl]amine;
2-((trans)-2-(4-(4-cyanobenzyloxy)phenyl)cyclopropylamino)acetamide;
2-((trans)-2-(4-(3-cyanobenzyloxy)phenyl)cyclopropylamino)acetamide;
2-((trans)-2-(4-(benzyloxy)phenyl)cyclopropylamino)acetamide;
2-((trans)-2-(4-(4-fluorobenzyloxy)phenyl)cyclopropylamino)acetamide;
2-((trans)-2-(4-(3-fluorobenzyloxy)phenyl)cyclopropylamino)acetamide;

2-((trans)-2-(4-(3-chlorobenzyloxy)phenyl)cyclopropylamino)acetamide;
2-((trans)-2-(4-(4-chlorobenzyloxy)phenyl)cyclopropylamino)acetamide;
2-((trans)-2-(4-(3-bromobenzyloxy)phenyl)cyclopropylamino)acetamide;
2-((trans)-2-(4-(3,5-difluorobenzyloxy)phenyl)cyclopropylamino)acetamide;
2-((trans)-2-(4-phenethoxyphenyl)cyclopropylamino)acetamide;
2-((trans)-2-(3'-(trifluoromethyl)biphenyl-4-yl)cyclopropylamino)acetamide; and
2-((trans)-2-(3'-chlorobiphenyl-4-yl)cyclopropylamino)acetamide;

or a pharmaceutically acceptable salt thereof.

9. The method according to claim 2, wherein the cyclopropylamine acetamide derivative or the cyclopropylamine derivative is selected from the group consisting of:

N-cyclopropyl-2-{[(trans)-2-phenylcyclopropyl]amino}acetamide;
2-{[(trans)-2-phenylcyclopropyl]amino}acetamide;
N-cyclopropyl-2-{[(trans)-2-phenylcyclopropyl]amino}propanamide;
2-{[(trans)-2-phenylcyclopropyl]amino}-N-prop-2-ynylacetamide;
N-(2-morpholin-4-yl-2-oxoethyl)-N-[(trans)-2-phenylcyclopropyl]amine;
2-{[(trans)-2-phenylcyclopropyl]amino}propanamide;
Methyl 2-{[(trans)-2-phenylcyclopropyl]amino}propanoate;
1-(4-methylpiperazin-1-yl)-2-((trans)-2-phenylcyclopropylamino)ethanone;
1-(4-ethylpiperazin-1-yl)-2-((trans)-2-phenylcyclopropylamino)ethanone;
1-(4-benzylpiperazin-1-yl)-2-((trans)-2-phenylcyclopropylamino)ethanone;
2-((trans)-2-phenylcyclopropylamino)-1-(4-phenylpiperazin-1-yl)ethanone;
2-((trans)-2-(4-(benzyloxy)phenyl)cyclopropylamino)-1-(4-methylpiperazin-1-yl)ethanone;
2-((trans)-2-(1,1'-biphenyl-4-yl)cyclopropylamino)-1-(4-methylpiperazin-1-yl)ethanone;
2-((trans)-2-(4-(benzyloxy)phenyl)cyclopropylamino)-N-cyclopropylacetamide;
2-((trans)-2-(4-(3-fluorobenzyloxy)phenyl)cyclopropylamino)-1-(4-methylpiperazin-1-yl)ethanone;
2-((trans)-2-(4-(4-fluorobenzyloxy)phenyl)cyclopropylamino)-1-(4-methylpiperazin-1-yl)ethanone;
2-((trans)-2-(4-(3-chlorobenzyloxy)phenyl)cyclopropylamino)-1-(4-methylpiperazin-1-yl)ethanone;
1-(4-methylpiperazin-1-yl)-2-((trans)-2-(4-phenethoxyphenyl) cyclopropylamino)ethanone;
2-((trans)-2-(biphenyl-4-yl)cyclopropylamino)-1-(4-methylpiperazin-1-yl)ethanone;
N-[2-(4-methylpiperazin-1-yl)ethyl]-N-[(trans)-2-phenylcyclopropyl]amine;
N-cyclopropyl-N'-[(trans)-2-phenylcyclopropyl]ethane-1,2-diamine;
N,N-dimethyl-N'-(2-{[(trans)-2-phenylcyclopropyl]amino}ethyl)ethane-1,2-diamine;
(3R)-1-(2-{[(trans)-2-phenylcyclopropyl]amino}ethyl)pyrrolidin-3-amine;
(3S)—N,N-dimethyl-1-(2-{[(trans)-2-phenylcyclopropyl]amino}ethyl)pyrrolidin-3-amine;
(3R)—N,N-dimethyl-1-(2-{[(trans)-2-phenylcyclopropyl]amino}ethyl)pyrrolidin-3-amine;
N-[(trans)-2-phenylcyclopropyl]-N-(2-piperazin-1-ylethyl)amine;
N,N-diethyl-N'-[(trans)-2-phenylcyclopropyl]ethane-1,2-diamine;
N-[(trans)-2-phenylcyclopropyl]-N-(2-piperidin-1-ylethyl)amine;
(trans)-2-(4-(benzyloxy)phenyl)-N-(2-(4-methylpiperazin-1-yl)ethyl)cyclopropanamine;
(trans)-N-(2-(4-methylpiperazin-1-yl)ethyl)-2-(3'-(trifluoromethyl)biphenyl-4-yl)cyclopropanamine;
(trans)-2-(3'-chlorobiphenyl-4-yl)-N-(2-(4-methylpiperazin-1-yl)ethyl)cyclopropanamine;
(R)-1-(2-((trans)-2-(3'-(trifluoromethyl)biphenyl-4-yl)cyclopropylamino)ethyl)pyrrolidin-3-amine;
$N^1$-cyclopropyl-$N^2$-((trans)-2-(3'-(trifluoromethyl)biphenyl-4-yl)cyclopropyl)ethane-1,2-diamine;
N-4-fluorobenzyl-N-{(trans)-2-[4-(benzyloxy)phenyl]cyclopropyl}amine;
N-4-methoxybenzyl-N-{(trans)-2-[4-(benzyloxy)phenyl]cyclopropyl}amine;
N-benzyl-N-{(trans)-2-[4-(benzyloxy)phenyl]cyclopropyl}amine,
N-[(trans)-2-phenylcyclopropyl]amino-methyl)pyridin-3-ol;
N-[(trans)-2-phenylcyclopropyl]-N-(3-methylpyridin-2-ylmethyl)amine;
N-[(trans)-2-phenylcyclopropyl]-N-(4-chloropyridin-3-ylmethyl)amine;
N-[(trans)-2-phenylcyclopropyl]-N-(4-trifluoromethylpyridin-3-ylmethyl)amine;
N-(3-methoxybenzyl)-N-[(trans)-2-phenylcyclopropyl]amine;
N-[(trans)-2-phenylcyclopropyl]-N-(quinolin-4-ylmethyl)amine;
N-(2-fluorobenzyl)-N-[(trans)-2-phenylcyclopropyl]amine;
N-(3-fluorobenzyl)-N-[(trans)-2-phenylcyclopropyl]amine;
N-[(trans)-2-phenylcyclopropyl]-N-(3,4-dichloro-1-phenylmethyl)amine;
N-[(trans)-2-phenylcyclopropyl]-N-(5-bromo-thiophen-2-ylmethyl)amine;
N-[(trans)-2-phenylcyclopropyl]-N-(3-bromo-thiophen-2-ylmethyl)amine;
N-[(trans)-2-phenylcyclopropyl]-N-(thiophen-2-ylmethyl)amine;
N-[(trans)-2-phenylcyclopropyl]-N-(1,3-thiazol-2-ylmethyl)amine;
N-[(trans)-2-phenylcyclopropyl]-N-(pyridin-4-ylmethyl)amine;
N-[(trans)-2-phenylcyclopropyl]-N-(pyridin-3-ylmethyl)amine;
N-[(trans)-2-phenylcyclopropyl]-N-(pyridin-2-ylmethyl)amine;
[(trans)-2-phenylcyclopropyl]-N-[4-(trifluoromethyl)benzyl]amine;
({[(trans)-2-phenylcyclopropyl]amino}methyl)benzonitrile;
N-(4-fluorobenzyl)-N-[(trans)-2-phenylcyclopropyl]amine;
N-[(trans)-2-phenylcyclopropyl]-N-(3-bromo-pyridin-2-ylmethyl)amine;
N-4-cyanobenzyl-N-{(trans)-2-[4-(benzyloxy)phenyl]cyclopropyl}amine;
N-4-[(benzyloxy)-benzyl]-N-[(trans)-2-(4-phenyl)cyclopropyl]amine;

2-((trans)-2-(4-(4-cyanobenzyloxy)phenyl)cyclopropylamino)acetamide;
2-((trans)-2-(4-(3-cyanobenzyloxy)phenyl)cyclopropylamino)acetamide;
2-((trans)-2-(4-(benzyloxy)phenyl)cyclopropylamino)acetamide;
2-((trans)-2-(4-(4-fluorobenzyloxy)phenyl)cyclopropylamino)acetamide;
2-((trans)-2-(4-(3-fluorobenzyloxy)phenyl)cyclopropylamino)acetamide;
2-((trans)-2-(4-(3-chlorobenzyloxy)phenyl)cyclopropylamino)acetamide;
2-((trans)-2-(4-(4-chlorobenzyloxy)phenyl)cyclopropylamino)acetamide;
2-((trans)-2-(4-(3-bromobenzyloxy)phenyl)cyclopropylamino)acetamide;
2-((trans)-2-(4-(3,5-difluorobenzyloxy)phenyl)cyclopropylamino)acetamide;
2-((trans)-2-(4-phenethoxyphenyl)cyclopropylamino)acetamide;
2-((trans)-2-(3'-(trifluoromethyl)biphenyl-4-yl)cyclopropylamino)acetamide; and
2-((trans)-2-(3'-chlorobiphenyl-4-yl)cyclopropylamino)acetamide;
or a pharmaceutically acceptable salt thereof.

\* \* \* \* \*